(12) United States Patent
Dourdeville et al.

(10) Patent No.: US 9,618,128 B2
(45) Date of Patent: Apr. 11, 2017

(54) METHOD AND APPARATUS FOR SAMPLE INJECTION IN LIQUID CHROMATOGRAPHY

(71) Applicant: Waters Technologies Corporation, Milford, MA (US)

(72) Inventors: Theodore A. Dourdeville, Providence, RI (US); Russell L. Keene, Sudbury, MA (US); Theodore D. Ciolkosz, Plymouth, MA (US); James E. Usowicz, Webster, MA (US)

(73) Assignee: Waters Technologies Corporation, Milford, MA (US)

( * ) Notice: Subject to any disclaimer, the term of this patent is extended or adjusted under 35 U.S.C. 154(b) by 39 days.

(21) Appl. No.: 14/529,947

(22) Filed: Oct. 31, 2014

(65) Prior Publication Data
US 2015/0047730 A1    Feb. 19, 2015

Related U.S. Application Data

(60) Continuation of application No. 13/227,078, filed on Sep. 7, 2011, now Pat. No. 8,881,582, which is a
(Continued)

(51) Int. Cl.
*F16K 11/085* (2006.01)
*G01N 30/20* (2006.01)

(52) U.S. Cl.
CPC .......... *F16K 11/0853* (2013.01); *G01N 30/20* (2013.01); *G01N 2030/201* (2013.01);
(Continued)

(58) Field of Classification Search
CPC ................. F16K 11/074; G01N 30/20; Y10T 137/86871; Y10T 137/86501; Y10T 137/86863
(Continued)

(56) References Cited

U.S. PATENT DOCUMENTS 3,223,123 A * 12/1965 Young ...................... F16K 3/04
137/625.46
3,368,385 A *  2/1968 Harvey, Jr. ............ G01N 30/20
376/245
(Continued)

FOREIGN PATENT DOCUMENTS

EP          0 409 522 A2    1/1991
JP          52-073187 A     6/1977
(Continued)

OTHER PUBLICATIONS

International Preliminary Report on Patentability PCT/US2006/003248 (issued Jul. 31, 2007).*
(Continued)

*Primary Examiner* — Michael R Reid
*Assistant Examiner* — Christopher Ballman
(74) *Attorney, Agent, or Firm* — Waters Technologies Corporation

(57) ABSTRACT

The present invention provides a method and apparatus for substantially eliminating destructive transients of pressure or flow rate which can degrade the efficiency and useful lifetime of chromatography columns. The present invention enables a substantially constant flow of mobile phase liquid to be maintained through the chromatography system by eliminating the flow blockage interval associated with the actuation of sample injection valves. The present invention further provides a method to reduce the pressure and flow rate transients associated with pressurization of the sample loop contents when the sample loop is introduced to chromatography system delivery pressure.

14 Claims, 21 Drawing Sheets

Related U.S. Application Data division of application No. 11/814,574, filed as application No. PCT/US2006/003248 on Jan. 31, 2006, now Pat. No. 8,047,060.

(60) Provisional application No. 60/648,540, filed on Jan. 31, 2005.

(52) U.S. Cl.
CPC .. *G01N 2030/202* (2013.01); *G01N 2030/207* (2013.01); *Y10T 137/0396* (2015.04); *Y10T 137/86871* (2015.04)

(58) Field of Classification Search
USPC .................. 137/625.11, 625.46, 625.47
See application file for complete search history.

(56) References Cited

U.S. PATENT DOCUMENTS

| | | | |
|---|---|---|---|
| 3,916,692 A | 11/1975 | Abrahams et al. | |
| 4,158,630 A | 6/1979 | Stearns | |
| 4,300,393 A | 11/1981 | Stearns | |
| 4,367,645 A * | 1/1983 | Froment | G01N 30/20 73/23.38 |
| 4,444,066 A * | 4/1984 | Ogle | G01N 30/20 73/61.56 |
| 4,506,558 A | 3/1985 | Bakalyar | |
| 4,625,569 A | 12/1986 | Toei et al. | |
| 4,810,392 A * | 3/1989 | Fulton | G01N 30/20 210/656 |
| 4,939,943 A | 7/1990 | Strohmeier | |
| 5,010,921 A | 4/1991 | Nohl | |
| 5,207,109 A | 5/1993 | Olsen | |
| 6,012,487 A * | 1/2000 | Hauck | F16K 11/0743 137/625.11 |
| 6,012,488 A | 1/2000 | Nichols | |
| 6,129,840 A | 10/2000 | Kitaoka | |
| 6,155,123 A | 12/2000 | Bakalyar | |
| 6,382,035 B1 | 5/2002 | Nichols | |
| 6,453,946 B2 | 9/2002 | Nichols et al. | |
| 6,490,938 B1 * | 12/2002 | Abdel-Rahman | G01N 30/20 73/863.72 |
| 6,502,448 B1 * | 1/2003 | Rapkin | G01N 30/62 210/198.2 |
| 6,672,336 B2 | 1/2004 | Nichols | |
| 6,874,354 B2 | 4/2005 | Cueni et al. | |
| 7,195,229 B2 | 3/2007 | Maeda | |
| 7,503,203 B2 | 3/2009 | Gamache et al. | |
| 7,574,901 B2 | 8/2009 | Iwata | |
| 8,047,060 B2 | 11/2011 | Dourdeville et al. | |
| 8,312,762 B2 | 11/2012 | Fadgen et al. | |
| 8,382,979 B2 | 2/2013 | Maeda et al. | |
| 8,881,582 B2 | 11/2014 | Dourdeville et al. | |
| 2001/0035516 A1 * | 11/2001 | Nichols | F16K 11/074 251/368 |
| 2004/0020542 A1 * | 2/2004 | Cueni | G01N 30/20 137/625.31 |
| 2004/0178133 A1 * | 9/2004 | Deguchi | G01N 30/20 210/198.2 |
| 2007/0251302 A1 | 11/2007 | Iwata | |
| 2009/0050212 A1 | 2/2009 | Dourdeville et al. | |
| 2009/0145205 A1 | 6/2009 | Hochgraeber et al. | |
| 2010/0281959 A1 | 11/2010 | Berndt | |
| 2012/0132013 A1 | 5/2012 | Glatz et al. | |
| 2013/0056084 A1 | 3/2013 | Dourdeville et al. | |

FOREIGN PATENT DOCUMENTS

| | | |
|---|---|---|
| JP | 55-030545 A | 3/1980 |
| JP | 59-013754 U | 1/1984 |
| JP | 60-143279 A | 7/1985 |
| JP | 60-143279 U | 9/1985 |
| JP | 61-174669 U | 10/1986 |
| JP | 62-056858 A | 3/1987 |
| JP | 63-080377 U | 5/1988 |
| JP | 64-044462 U | 3/1989 |
| JP | 03-019962 U | 2/1991 |
| JP | 05-273187 A | 10/1993 |
| JP | 10-151315 A | 6/1998 |
| JP | 11-230385 A | 8/1999 |
| JP | 2000-074893 A | 3/2000 |
| JP | 2001-255316 A | 9/2001 |
| JP | 2002-310311 A | 10/2002 |
| JP | 2003-107065 A | 4/2003 |
| JP | 2005-121384 A | 5/2005 |
| JP | 2006-308056 A | 11/2006 |
| JP | 2007-292620 A | 11/2007 |
| WO | 02/39105 A1 | 5/2002 |
| WO | 2006/083776 A2 | 8/2006 |
| WO | 2010/139359 A1 | 12/2010 |

OTHER PUBLICATIONS

Extended European Search Report for Application No. 06719892.9, dated Sep. 7, 2010.
International Search Report for Application No. PCT/US2006/003248, mailed Jul. 9, 2007.
International Written Opinion for Application No. PCT/US2006/003248, mailed Jul. 9, 2007.
Japanese Office Action for Application No. JP 2007-553330, mailed Jan. 10, 2012 (11 pages).
Translation Notice of Rejection for Japanese Patent Application No. 2012-153234, mailing dated of Feb. 4, 2014 (4 pages).

\* cited by examiner

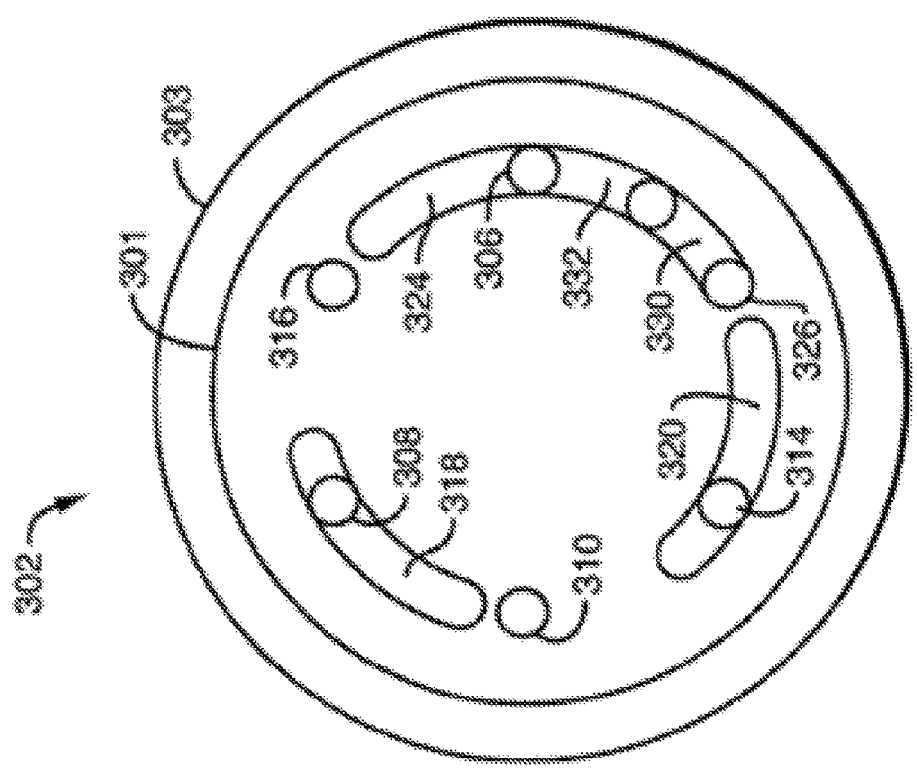

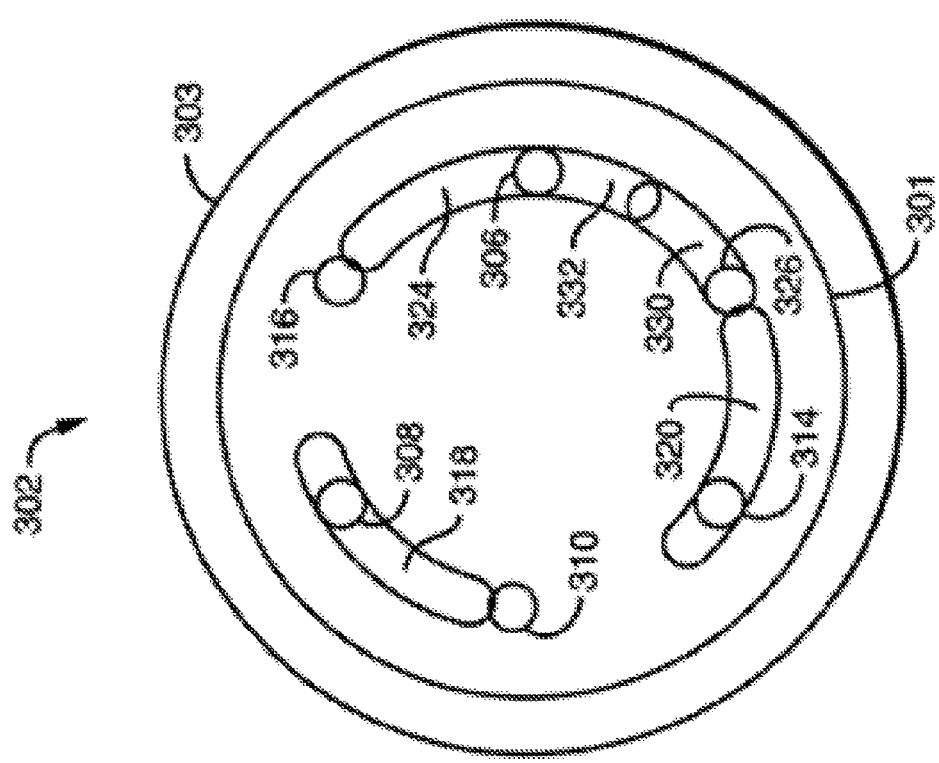

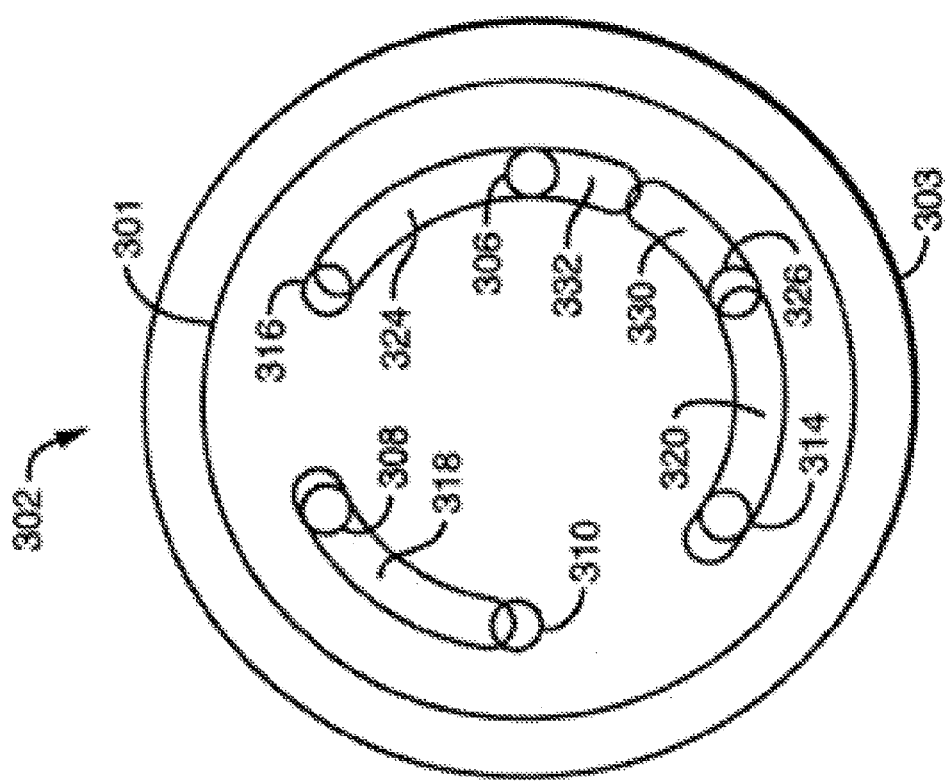

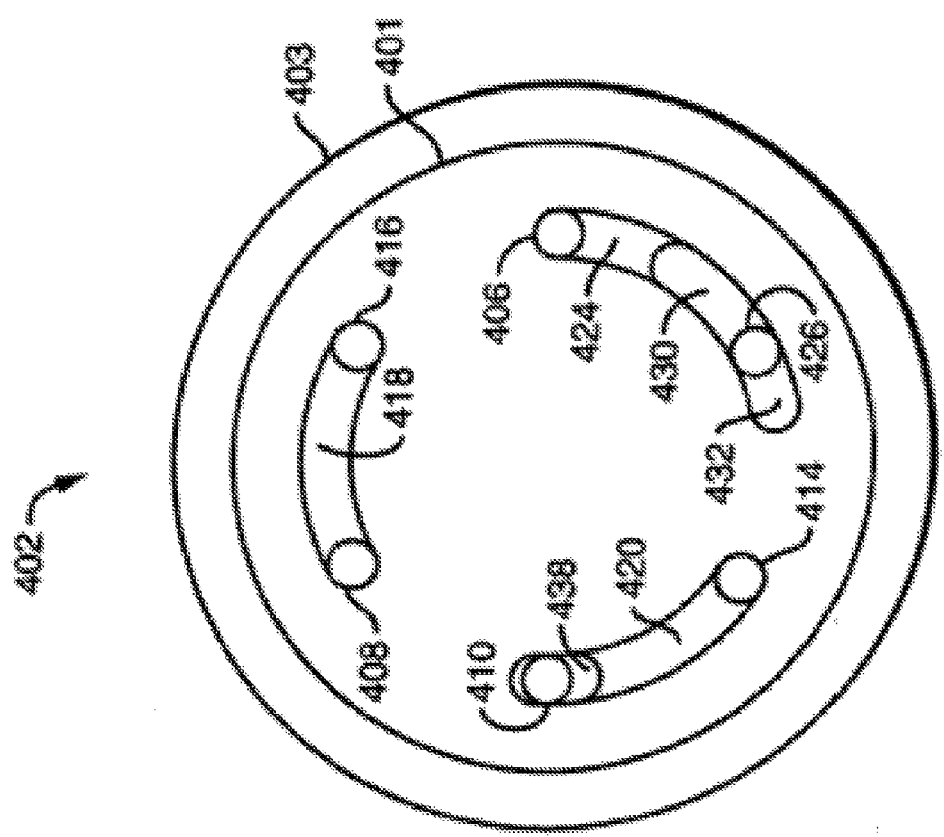

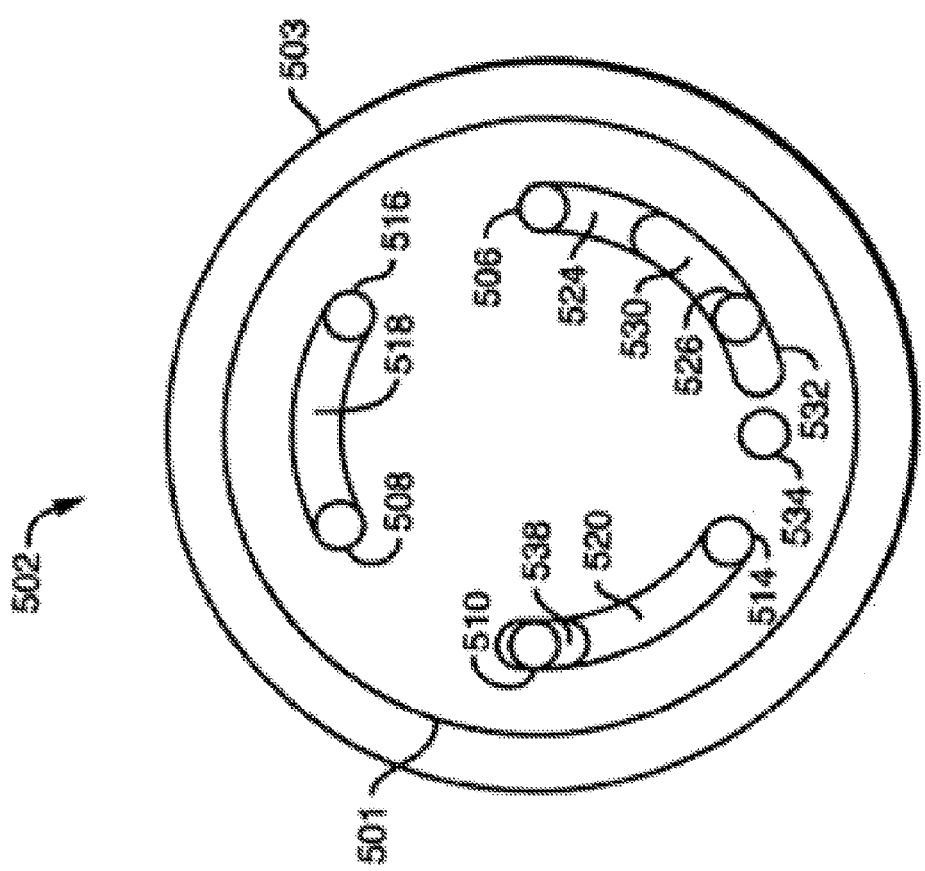

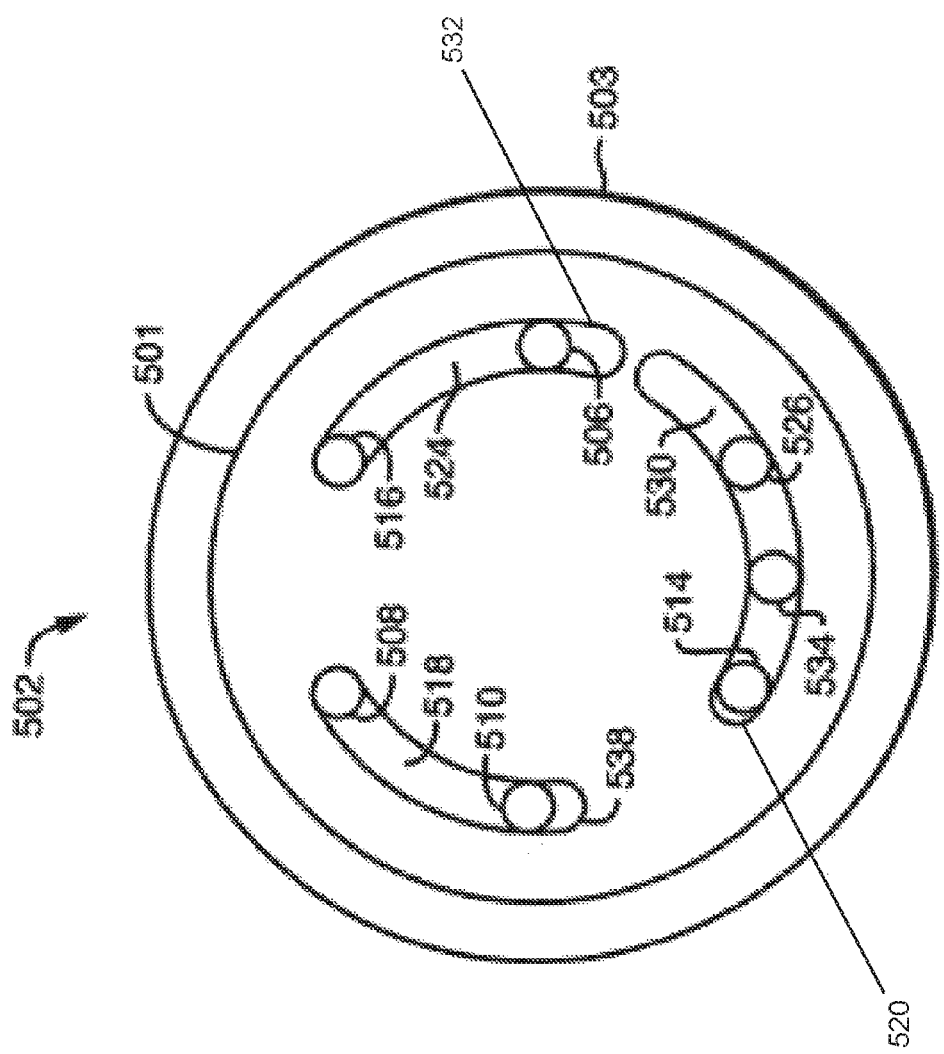

METHOD AND APPARATUS FOR SAMPLE INJECTION IN LIQUID CHROMATOGRAPHY

CROSS REFERENCE TO RELATED APPLICATIONS

This application is a continuation of U.S. application Ser. No. 13/227,078 filed Sep. 7, 2011, which a division of U.S. application Ser. No. 11/814,574, filed Mar. 28, 2008, which is the National Stage of International Application No. PCT/US2006/03248, filed on Jan. 31, 2006, which claims priority to and benefit of U.S. Provisional Patent Application No. 60/648,540, filed Jan. 31, 2005. The entire contents and teachings of each of each of the aforementioned applications are hereby expressly incorporated herein by reference in their entirety.

FIELD OF THE INVENTION

The present invention relates to high pressure liquid chromatography, particularly to a sample injection subsystem used to introduce sample for analysis by the high pressure liquid chromatography system.

BACKGROUND OF THE INVENTION

The introduction of sample into a high pressure liquid chromatography ("HPLC") analysis system is normally accomplished through the operation of an apparatus termed a sample injector, which is interposed in the HPLC system fluid circuit downstream of the mobile phase delivery pump(s) and upstream of the analytical column. This configuration accomplishes a substantially direct introduction of sample to the head or inlet end of the analytical column. Variants of this simple configuration are known in the art, an example being a "sample trapping" configuration where the sample injector may reside between an auxiliary pump and a dedicated sample trapping column, and where the sample trapping fluid circuit may be isolated from the analytical column fluid circuit during the trap loading interval. At the completion of the trap loading process, the trap column is then switched into the analytical column fluid circuit by the action of one or more switching valves. Following the switching step, sample is eluted from the trapping column onto the analytical column by the analytical mobile phase, thereby enabling analyte separation to be performed on the analytical column substantially as in the direct introduction mode. The sample trapping mobile phase may be selected to differ in composition and flow rate from the analytical mobile phase, as is known in the art. Similarly, the stationary phase used in the sample trapping column may be selected to differ from that used in the analytical column, also as known in the art.

In any case, the normal operation of the sample injector is to cause a liquid volume, which initially resides at a pressure substantially equal to atmospheric pressure, to be introduced into a mobile phase stream which is flowing, and which is at a relatively high pressure, typically in the range of thousands of pounds force per square inch (PSI) (tens of megaPascals (MPa)). The liquid volume which is introduced is typically a prescribed volume of a sample solution in which one or more sample analytes are dissolved. In some implementations, the sample volume may be bracketed by small air-gaps, which are utilized to minimize the broadening of the sample zone as the sample is conveyed within a fluid conduit from a sample vial toward or to the point of injection.

The actual injection operation which introduces a liquid sample volume into a high pressure mobile phase delivery stream is typically carried out by the action of one or more valves capable of redirecting the mobile phase flow. Two general approaches to sample injector implementation have been widely utilized over the past several decades. One approach is the multi-port rotary shear seal valve, commercially available from several vendors including Valco Instruments Company Inc. (VICI, Houston, Tex.), Upchurch Scientific Division of Scivex Corporation (Oak Harbor, Wash.), and Rheodyne LLC (Rohnert Park, Calif.). The other general approach is the resistive bypass injector configuration, in both manually-actuated and automated forms.

A six-port rotary shear seal valve provided with an external sample loop is a common configuration used to perform sample injection in conventional HPLC. The use of such a valve is promoted by its relatively small overall size, moderate cost, and relative simplicity of operation. In common with many other multi-port shear seal valves, the conventional six-port rotary shear seal injection valve integrates multiple stream-switching elements into a single rotor-stator assembly, thereby enabling coordinated actuation of the plurality of valve elements by a single actuating mechanism such as an electric motor.

Related to the six-port, external-loop shear seal valve is another common variant, the four-port, internal-loop valve, which shares with the six-port valve the desirable attributes of small size, moderate cost, and simplicity of operation. The reduction in external port count from six to four is a result of the sample loop being implemented internal to the valve, thereby eliminating the need for the two external ports used for the attachment of an external sample loop.

Both the four-port and six-port valve types, when used as sample injection valves, are essentially two-state devices. In the LOAD state, fluid communication between the mobile phase pump and the column is enabled while the sample loop is maintained in fluid communication with a sample aspiration path. In the INJECT state, fluid communication between pump and column is established through the sample loop, enabling the transport of the loop contents toward the column. An undesirable attribute shared by conventional rotary shear seal injection valves is that during transition between the LOAD and INJECT state, or between the INJECT and LOAD state, the flow path between pump and column is temporarily blocked. This behavior is often described as a "break-before-make" type of switching.

Even at conventional HPLC flow rates and pressures, break-before-make switching of the fluid path internal to the sample injection valve gives rise to very significant flow and pressure transients in the mobile phase stream. These transients arising from flow blockage and reinstatement occur during both the INJECT-to-LOAD and the LOAD-to-INJECT valve state transitions. During the time interval in which the pump-to-column flow is obstructed, the pump continues to source mobile phase into a now dead-ended fluid path, causing the liquid pressure in the fluid circuit upstream of the obstruction to rise. At the same time, the column is continuing to sink mobile phase from the fluid circuit downstream of the blockage, in accordance with the pressure differential imposed across the column, and the resistance to flow exhibited by the column. In circumstances where a meaningful additional resistance to flow exists between the column outlet and the ultimate liquid discharge point (typically discharging to atmosphere downstream of a detector), the sink flow rate will be determined by the sum of the column and additional series resistances, and the pressure differential asserted over that collective resistance. For a conventional rotary shear seal injection valve with a typical motorized actuator, the timeframe during which the upstream and downstream fluid circuits are isolated may readily be in the range of approximately one hundred to several hundred milliseconds.

Because of the relative stiffness of liquids, a flow blockage of approximately one hundred to several hundred milliseconds duration can lead to a significant pressure differential being imposed across the injection valve. Specifically, the upstream and downstream fluid circuits may depart from one another in internal pressure at rates corresponding to tens of thousands of PSI per second (hundreds of MPa per second). When the valve nears completion of its state transition, the previously-isolated upstream and downstream fluid circuits are restored to a condition of fluid communication. The reinstatement of fluid communication within the valve is immediately followed by an aggressive exchange of liquid from the higher-pressure to the lower-pressure circuit. The rate-of-change of pressure observed near the column head, during the initial convergence of pressures, may exceed one million PSI per second (7000 MPa per second), for an interval of one to several milliseconds. The initial pressure transient may be followed by one or more cycles of damped ringing attributable to the combined effects of fluid inertance, fluid capacitance, and resistance to fluid flow.

These transients typically become more severe as system operating pressure increases, or as the pre-column system volume decreases (the latter tending to reduce the parasitic fluid capacitance available to cushion the effect). Ongoing interest within the HPLC community in achieving higher separation efficiencies and shorter analysis times has led to the development and commercial adoption of column packing particles as small as approximately 1.5 micrometers in mean diameter. Effective use of analytical columns packed with such small particles typically requires system operation in a pressure regime above that of conventional HPLC, commonly termed very high pressure liquid chromatography ("VHPLC"). Conditions associated with VHPLC system operation, which may include mobile phase delivery pressures of 10000 PSIG (70 MPa) or higher, and very low pre-column system volume, are substantially the conditions which exacerbate the transient.

Abrupt transients of liquid flow rate and liquid pressure in the vicinity of the column head can be extremely disruptive to HPLC columns. The disruptive effects upon the column are most readily observed as a loss of achievable separation efficiency for a defined separation which is performed repeatedly, or as a change (typically an increase) in the resistance to flow exhibited by the column, for a defined operating condition corresponding to a prescribed mobile phase composition, flow rate, and column temperature.

Modifications to known rotary shear seal injection valves include a feature intended to reduce the time duration of the flow blockage during valve state transition. In these valves a groove or channel extends from the pump port on the valve stator toward the column port, whereby the connection time between the pump and the column is prolonged or extended over the connection time associated with an unmodified valve undergoing state transition. In one commercial embodiment, a typical time duration of flow blockage of about 50 milliseconds is achieved. Unfortunately, in VHPLC system operation, even a 50 millisecond flow blockage can lead to dramatic column impairment. The transients arising from intermittent flow blockage are typically rapid events with characteristic timeframes measured in the range of one to several milliseconds, and can be produced by flow blockages of similarly short duration. In that context, a 50 millisecond break-before-make switching behavior is highly significant, and a valve exhibiting that duration of complete flow blockage is substantially inadequate to address the column degradation problem.

The resistive bypass sample injection technique of Abrahams and Hutchins circumvents the direct blockage of flow during sample injection by providing a parallel fluid pathway between pump and column which is never obstructed by valve actuation. In the LOAD state of a resistive bypass injector, pump-to-column flow is conveyed entirely through the bypass path. In this state, the sample loop is isolated by diaphragm or other type valve elements from system pressure, allowing the sample loop to be loaded with a sample residing at substantially atmospheric pressure. During transition to the INJECT state, the valves previously isolating the sample loop are opened, exposing the sample loop contents to system pressure. In the INJECT state, the fluid path encompassing the sample loop resides in parallel with the constantly-enabled bypass path. A critical aspect of the valve implementation is the selection of the relative resistance to flow of these two parallel fluid paths. In one implementation, the tubing internal diameters and lengths are selected such that the bypass path has a resistance to flow which is about 32 times higher than that of the sample loop path. With this configuration, when the valve resides in the INJECT state, approximately 97 percent of the pump flow is sustained through the sample loop, with the remaining 3 percent bypassing the sample loop. The use of less than 100 percent of the pump flow to convey the sample from the loop will cause the injected sample to emerge from the loop over a longer interval of time, and to become diluted by the bypass flow. In the example above, the sample band would emerge from the injector in a volume approximately 1.03 times larger than that which would be obtained in the absence of any bypass flow. Because the characteristic peak width of an injection impulse is an important figure-of-merit of an HPLC sample injector, effort is expended to keep the bypass percentage as low as possible in light of other design considerations. Among those considerations are the relative rates at which the sample and bypass paths are purged with fresh mobile phase. In a gradient mode of chromatography, the mobile phase compositional gradient will typically pass through the sample injector, and therefore will negotiate both the sample and the bypass paths when the valve is in the INJECT state. Poor matching of the purging rates of these two parallel paths can lead to corruption of the gradient profile.

Another consideration with the resistive bypass injection technique is that the resistance of the bypass path is additive in series to the column and other system resistances when the valve is in the LOAD state (that is, when 100 percent of the pump flow is being directed through the bypass path). When the valve is transitioned to the INJECT state, the resistance of the bypass path is largely circumvented, as that path is placed in parallel with a sample loop path having a resistance typically some thirty times lower. Thus the overall system resistance to flow can be observed to shift between two values, corresponding to the LOAD and the INJECT states of the sample injector, respectively. These shifts occur over timeframes governed by the overall system hydraulic time constant.

In addition to the above considerations, the resistive bypass injector as implemented by Abrahams and Hutchins is generally more complex and more expensive to manufacture than a conventional multi-port rotary shear seal valve.

The transients discussed above are transients arising from the temporary blockage of flow within an HPLC or VHPLC system as a result of injector actuation. An additional aspect of sample injection is the transient behavior associated with the pressurization of the sample loop contents, corresponding to the charging of the sample loop fluid capacitance. The magnitude of this transient is a function of sample loop volume, air gap volume (if used), system operating pressure, and the compositions of the sample diluent and mobile phase. Its time-course is affected by the configuration of the fluid conduits upstream and downstream of the sample injector. Whereas the transient in mobile phase flow or pressure associated with flow blockage is substantially similar for both state transitions of the sample injector (LOAD to INJECT and INJECT to LOAD), the loop charging transient is manifested in the LOAD to INJECT transition. The behavior arises from the fluid current inrush which pressurizes the sample loop contents from atmospheric pressure to system operating pressure, typically in a timeframe of one to several milliseconds.

Depending upon the configuration of the upstream and downstream fluid conduits, that inrush current may be transiently sourced from both the column head and pump capacitances. When the sample loop is taken off-line during the INJECT to LOAD transition, a rapid decompression of the pressurized loop contents occurs, but that discharge current is directed toward other system components and is substantially invisible to the column. While the resistive bypass injector configuration substantially circumvents the problem of flow blockage transients, it shares with the shear seal injection valve the undesirable characteristic of causing a loop charging transient when the un-pressurized sample is exposed to system pressure. In a VHPLC system, the loop charging transient may be the dominant transient associated with sample injection, and under worst-case conditions of a large sample loop with air-gaps present, may result in a nearly instantaneous and substantially complete depressurization of the column head, with attendant destructive impact upon the column.

SUMMARY OF INVENTION

The present invention provides a method and apparatus for substantially eliminating destructive pressure transients arising from the operation of the sample injector.

An illustrative embodiment of the present invention uses a rotary shear seal valve to direct the flow of mobile phase liquid within a portion of the fluid circuit between the pump and column. Arc-shaped rotor channels are defined in the valve rotor, including a sample channel, a loop channel, and a column channel. These rotor channels interact cooperatively with fluid ports and port channel extensions which reside in the valve stator. These stator ports are uniquely identified on the basis of their respective connectivities to system components external to the valve stator. These system components include a mobile phase delivery pump, a chromatography column, a sample needle, a sample aspiration syringe assembly, and a sample loop having respective upstream and downstream ends. In the rotor position corresponding to the LOAD state of the valve, the rotor sample channel connects the sample needle port with a downstream sample loop port. The rotor loop channel connects an upstream sample loop port with a syringe port. The rotor column channel connects a pump port and a column port. In this rotor position, sample can be aspirated into the sample loop while mobile phase is delivered from the pump to the column. The upstream and downstream ends of the sample loop are defined relative to the flow direction which conveys sample from the loop to the column when the valve is in the INJECT state.

In the rotor position corresponding to the INJECT state of the valve, the rotor channels are commutated about 60 degrees from their LOAD state positions, to establish communication between different ports. In the INJECT state, the rotor loop channel connects the pump port to the upstream loop port; the column channel connects the downstream loop port to the column port; and the sample channel connects the syringe port to the sample needle port. In this rotor position the sample loop contents are flushed toward the column by the mobile phase flow delivered from the pump. This illustrative embodiment includes modification of certain flow paths in the valve rotor and stator of a traditional rotary shear seal injection valve. Typically, a rotor channel spans only an arc sufficient to encompass the distal edges of the two ports on the stator for which fluid communication is intended. Elongation of the rotor column channel toward the loop channel interacts cooperatively with elongation of the stator pump port to ensure that pump-to-column flow is sustained throughout the state transition of the valve, thereby substantially eliminating the destructive transients that arise from the intermittent blockage of pump-to-column flow obtained with prior art shear seal valves.

The pump port on the stator, in this illustrative embodiment, has a first additional channel feature extending counter-clockwise from the pump port toward the column port. This channel, always in fluid communication with the pump port itself, interacts cooperatively with the rotor column channel to ensure that pump-to-column flow is enabled throughout the state transition of the valve. Specifically, upon valve transition from the LOAD to the INJECT state, direct fluid communication between the pump port and column port is terminated only after fluid communication is established between the pump port and the column port by way of the sample loop. Correspondingly, upon valve transition from the INJECT to the LOAD state, fluid communication between the pump port and column port, by way of the sample loop, is terminated only after a direct fluid communication path is established between the pump and column ports. Thus at least one flow path interconnecting the pump port and column port exists independent of valve state, including intermediate states where the valve rotor is either in motion or is arrested in transit between the two end states LOAD and INJECT. Avoidance of flow blockage eliminates the source of flow blockage transients, contributing significantly to the extension of the useful life of the column.

In another illustrative embodiment, the pump port on the stator has a second additional channel feature extending clockwise from the pump port toward the upstream sample loop port. This channel, always in fluid communication with the pump port itself, interacts cooperatively with the rotor loop channel during the LOAD to INJECT state transition to bias the valve timing such that the sample loop is deterministically pressurized from the direction of the upstream loop port. With an injection valve configured for last-in first-out ("LIFO") sample transport into and out of the sample loop, small sample volumes that are migrated only a short distance into a relatively large sample loop, and which may optionally be bracketed by air-gap volumes, may be subjected to less zone broadening when this direction of sample loop pressurization is employed.

Another illustrative embodiment uses the same extended rotor column channel and first additional stator pump port channel of a previous embodiment and additionally features an extended rotor loop channel. The extension of the rotor loop channel is used to bias the valve timing such that when the valve is transitioned from the INJECT to the LOAD state, fluid communication is established between the sample loop upstream port and the syringe port prior to the establishment of fluid communication between the sample loop downstream port and the sample needle port. This bias allows for the fluid current associated with sample loop depressurization to be directed toward the syringe assembly as opposed to being directed toward the sample needle, or as opposed to being shared between the fluid circuits of the syringe assembly and the sample needle. Uncontrolled displacement of liquid within the sample needle fluid circuit can be detrimental in certain modes of operation of the sample injector. The timing bias achieved by extension of the rotor loop channel allows the sample loop fluid capacitance to initially discharge toward the syringe assembly, resulting in a partial charging or pressurization of that fluid circuit. According to the invention the valve geometry does not block the pump-to-column flow, the valve rotor motion can be arrested in this position where fluid continuity between the sample loop and the syringe assembly is enabled. In this rotor orientation, the syringe assembly can be actuated so as to return the syringe and sample loop to a pressure of substantially atmospheric pressure (0 PSIG). The valve rotor can subsequently be actuated to complete its transition to the position corresponding to the LOAD state of the valve. This sequence of events allows for fluid communication to be reestablished between the sample loop downstream port and the sample needle under conditions where substantially no pressure differential exists between the two, with the result that unintended displacement of liquid within the sample needle is substantially eliminated.

Reduction of the flow rate and pressure transients associated with sample injection can enhance the useful lifetime of the column, increasing the number of samples that may be separated before column performance degrades to the extent that column replacement is required.

According to the invention, it would be desirable to pressurize the contents of the sample loop to system operating pressure prior to introducing the sample loop contents online. Taken in conjunction with a valve that never blocks pump-to-column flow, an essentially transient-free sample injection would be accomplished. From a practical standpoint, it would be further desirable to avoid a separate pressurization subsystem. The inventive sample pressurization approach described herein accomplishes the above by utilizing the mobile phase pump to pressurize or charge the sample loop capacitance in parallel with mobile phase delivery to the column, during a defined interval of system operation. The timeframe for this sample pre-compression is chosen to be readily accommodated within the pump controller bandwidth, and is established by coupling the upstream end of an otherwise-isolated sample loop to the pump by way of a fluid current-limiting resistance. This is accomplished within a nominal 6-port injection valve configuration by arresting the valve rotor near the midpoint of the LOAD to INJECT transition, and by utilizing the rotor loop channel to establish fluid communication between the upstream sample loop port and an interposed (seventh) stator port neighboring the pump port.

The downstream sample loop port remains fluidically isolated from any other stator port. The additional, interposed port differs from the pump port in that its connection to the pump is accomplished with a fluid conduit having a selected resistance to mobile phase flow. Accordingly, the magnitude of the loop-pressurization flow rate can be made small compared to the column flow rate, requiring only modest incremental delivery from the pump to maintain the column flow rate substantially constant. Alternatively, the loop charging flow rate can be made sufficiently small that no compensatory action by the pump is required to prevent column degradation. In one embodiment, the time duration of the pre-compression interval is fixed, and is chosen so as to accomplish satisfactory pressurization of the largest realistically-expected loop capacitance, automatically addressing all smaller capacitances.

At the completion of this fixed pre-compression interval, the valve rotor is transitioned to the INJECT state, and sample injection occurs. Throughout the loop pressurization interval corresponding to a PRECOMPRESS state of the valve, mobile phase flow to the column is maintained by the appropriate configuration of flow channels within the rotor and stator of the valve. Because flow to the column is never obstructed, the valve can be maintained in the PRECOMPRESS state for whatever timeframe is deemed suitable or necessary for the pre-compression of the sample loop contents to occur. Another further illustrative embodiment in accordance with the present invention concerns the use of a bypass channel between the pump and the column, in conjunction with a rotary shear seal injection valve.

The bypass channel maintains fluid communication between the pump and the column independent of the state of the rotary shear seal valve. The existence of a bypass channel substantially eliminates the need for the rotor column channel extension and the need for the cooperative pump stator port first additional channel as described in the first embodiment above. The present embodiment takes advantage of the relative simplicity and small size of the rotary shear seal valve, and can also take advantage of the additional inventive features described in the embodiments above, including the ability to deterministically control the direction from which the sample loop is pressurized, the ability to accomplish controlled decompression of the sample loop contents through a preferred path, and the ability to achieve rate-limited pre-compression of the sample loop contents during the sample injection sequence.

The bypass channel embodiment differs from the other inventive shear seal sample injector embodiments in that a small amount of sample dilution occurs as a result of the bypassing of the valve. However, the magnitude of this dilution may be held to a manageable value, such as an approximately 3 percent dilution, by appropriate selection of the relative resistances of the bypass path and the sample loop path. The rotary shear seal valve contributes to an effective sample injector implementation because the internal flow paths may be constructed so as to be of low overall volume, and to be of relatively cleanly-swept geometry. Reduction in the overall liquid volume within the valve tends to minimize the extent to which perturbation of a gradient composition profile can occur, as a gradient profile is propagated through the sample injector.

Illustrative embodiments of the present invention reduce or substantially eliminate destructive transients of mobile phase flow rate or pressure associated with sample injection into HPLC or VHPLC systems, as well as sample loop compression transients. The substantial elimination of these two classes of transients can significantly improve the useful lifetime of both HPLC and VHPLC chromatography columns.

Another advantage of the present invention is the adaptability of the configurations of the rotor channels and stator ports and port channels. Various arrangements of extended channels in the rotor and expanded or extended ports in the stator can similarly substantially eliminate destructive transients of flow rate and pressure.

Yet a further advantage of the present invention is the ability to control the direction of compression of the sample loop contents during the sequence of events leading to sample injection into the high pressure mobile phase stream, in addition to controlling the direction of decompression of the sample loop contents when the loop is removed from the high pressure mobile phase stream and its contents are decompressed prior to the aspiration of a subsequent sample.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 3d is an axial view of a rotor-stator alignment of a valve depicted at 45 degrees counter-clockwise rotation in accordance with an embodiment of the invention;

FIG. 3e is an axial view of a rotor-stator alignment of a valve depicted at 50 degrees counter-clockwise rotation in accordance with an embodiment of the invention;

FIG. 3f is an axial view of a rotor-stator alignment of a valve depicted at 55 degrees counter-clockwise rotation in accordance with an embodiment of the invention;

FIG. 4a is an axial view of a rotor-stator alignment of another illustrative embodiment of a valve in accordance with the present invention, depicted at 0 degrees counter-clockwise rotation corresponding to the LOAD state of the valve;

FIG. 5a is an axial view of a rotor-stator alignment of an illustrative embodiment of a loop-pre-compressing valve with a seventh port, in accordance with the present invention, depicted at 0 degrees counter-clockwise rotation corresponding to the LOAD state of the valve;

FIG. 5c is an axial view of a rotor-stator alignment of an illustrative embodiment of a loop-pre-compressing valve with a seventh port, in accordance with the present invention, depicted at 60 degrees counter-clockwise rotation corresponding to the INJECT state of the valve;

DETAILED DESCRIPTION

Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Figure 1:
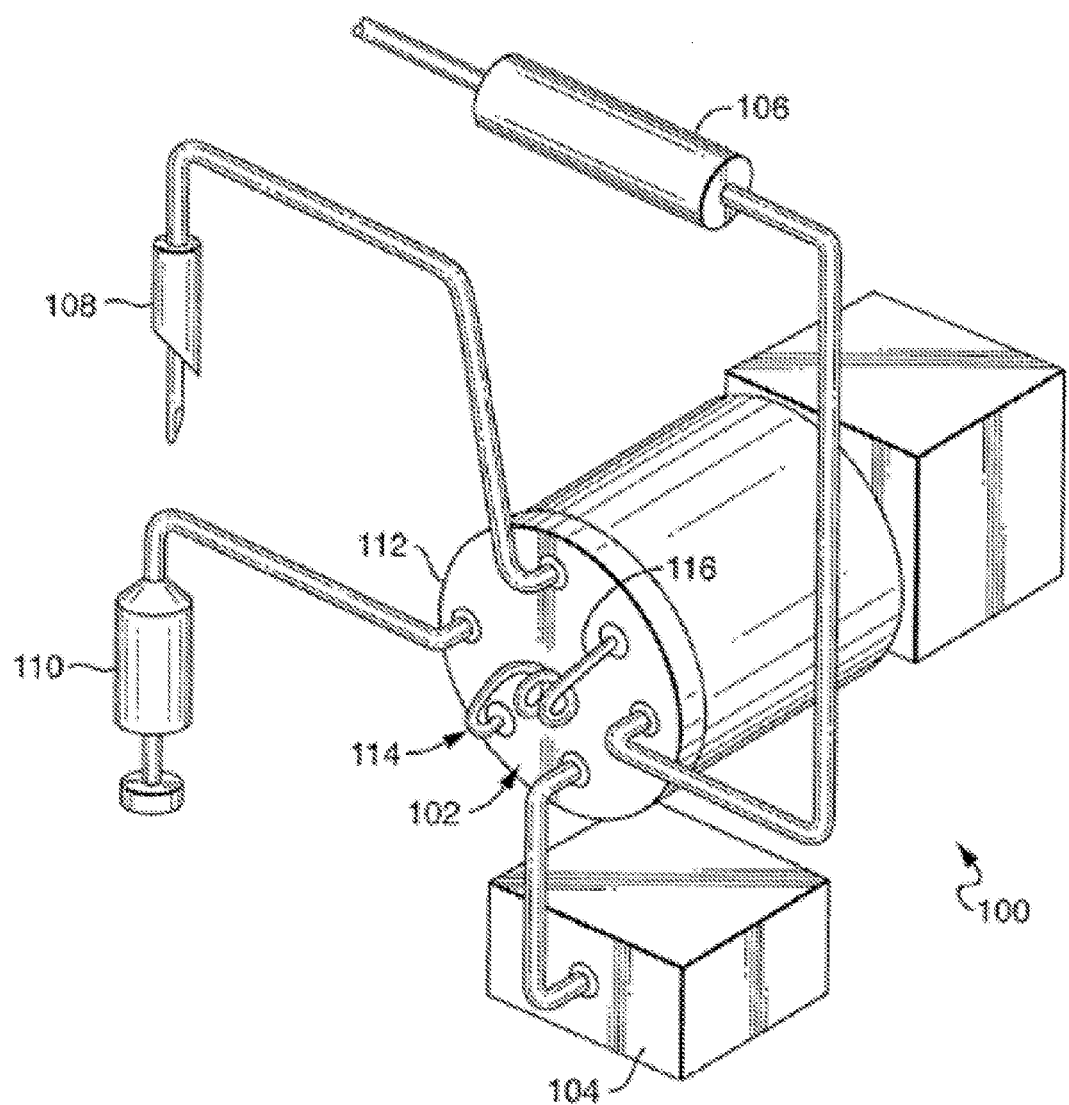
FIG. 1 is a block diagram of a high pressure liquid chromatography system according to the prior art.

Turning to FIG. 1, a simplified block diagram of a standard arrangement of an HPLC system 100 utilizing a rotary shear-seal injection valve 102 is shown. Rotary shear seal injection valve 102 is connected to a mobile phase pump 104. The pump 104 delivers mobile phase liquid through selected internal fluid pathways of rotary shear seal injection valve 102. A separation column 106 is also connected to the rotary shear seal injection valve. Separation column 106 acts in concert with the mobile phase to accomplish separation of the various sample components introduced into the mobile phase stream of HPLC system 100. A sample needle 108 is connected to rotary shear seal injection valve 102. The sample needle 108 may be inserted into a sample vial (not shown) for the purpose of in-taking an aliquot of a sample solution contained within the vial. Sample needle 108 is the entry point of sample solution into the sample uptake or aspiration path leading to external sample loop 112 of injection valve 102.

A syringe assembly 110 is connected to rotary shear seal injection valve 102. The syringe assembly 110 interacts cooperatively with injection valve 102 to control the uptake or aspiration of sample through sample needle 108, typically by causing a prescribed volumetric displacement of liquid within sample needle 108. External sample loop 112 residing in fluid communication with rotary shear seal injection valve 102 has an upstream loop end 114 and a downstream loop end 116. In the LOAD state of injection valve 102, syringe assembly 110 is in fluid communication with the upstream loop end 114 of external sample loop 112, while sample needle 108 is in fluid communication with downstream loop end 116. In this illustrative configuration, sample may be aspirated from a sample vial into sample loop 112 through the action of syringe assembly 110. With the injection valve in the LOAD state, fluid communication between pump 104 and column 106 exists such that mobile phase liquid can be supplied to the column.

When rotary shear seal injection valve 102 is transitioned to the INJECT state, the pattern of fluid communication internal to the valve is changed, redirecting the fluid flow. With injection valve 102 in the INJECT state, pump 104 is in fluid communication with the upstream loop end 114 of external sample loop 112, while column 106 is in fluid communication with downstream end 116 of sample loop 112. In this configuration, the mobile phase flow sourced from pump 104 propels any sample solution contained within external sample loop 112 toward separation column 106. In the INJECT state of injection valve 102, syringe assembly 110 is in fluid communication with sample needle 108.

Automated sample injectors as are well known in the art further utilize syringe assembly 110 to carry out washing of the sample needle and repositioning of the syringe piston in preparation for a subsequent injection. The internal resources (not shown) required within the syringe assembly 110 typically include one or more syringe cylinders, each cooperating with a corresponding piston responsive to a motorized actuator; a syringe manifold and selector valving which allows a syringe to be replenished with a working fluid or a selection of working fluids; a pressure transducer capable of monitoring the pressure internal to a syringe manifold or specific syringe cylinder, and optionally one or more relief or vent valves configured to vent pressure from a syringe assembly fluid circuit to atmosphere or to a specified fluid current sink.

Figure 2:
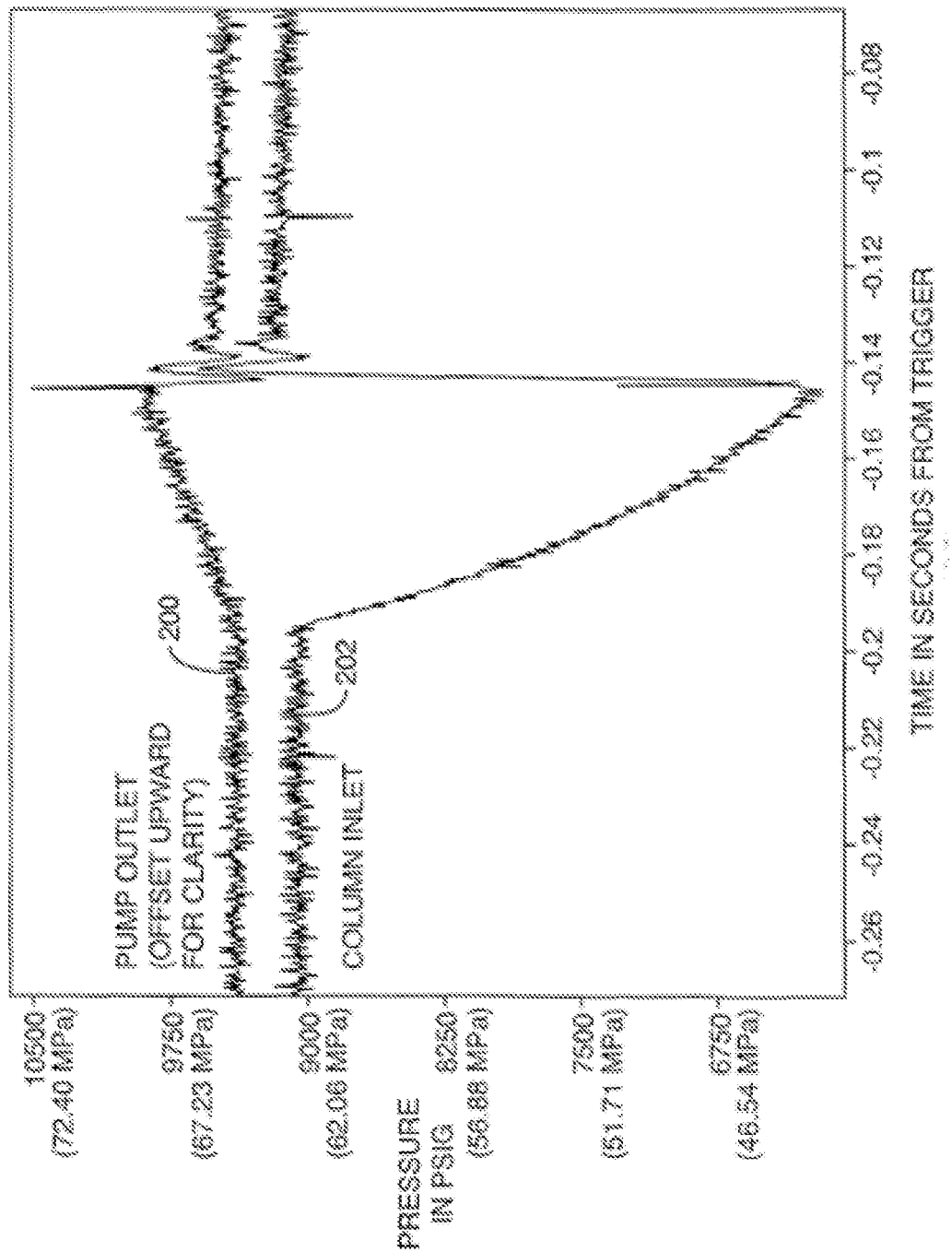
FIG. 2 is an illustration of mobile phase pressure measured upstream and downstream of an injector according to the prior art, during injector actuation.

FIG. 2 depicts a measured pressure transient caused by the actuation of a prior art rotary shear seal injection valve during valve state transition. Upstream pressure trace 200 is obtained from a low-volume pressure transducer located in the chromatography fluid circuit between the pump and the injection valve. Downstream pressure trace 202 is obtained from a second low-volume pressure transducer located in the fluid circuit between the injection valve and the column. Upstream pressure trace 200 has been offset upward by approximately 250 PSI (1.72 MPa) for clarity. The time interval from approximately −0.195 seconds to approximately −0.145 seconds corresponds to the flow blockage interval of the injection valve in use. During that flow blockage interval, the two pressure traces are observed to depart from one another, with upstream pressure trace 200 rising while downstream pressure trace 202 is falling.

The mean rate of departure over this approximately 50 millisecond interval is approximately 60,000 PSI (414 MPa) per second. This interval of pressure departure terminates when fluid communication is reestablished between the upstream and downstream fluid circuits. Over the subsequent several milliseconds, the two pressure traces are observed to converge rapidly. This convergence is followed by an interval of damped ringing which is a result of the combined effects of fluid inertance, fluid capacitance, and resistance to fluid flow within the fluid circuit connecting the pump with the injector and column. The maximum rate of change of pressure measured at the downstream pressure transducer during the pressure convergence interval is approximately 1.2 million PSI (8270 MPa) per second.

In FIGS. 3a-g, an illustrative embodiment of a sample injector according to the invention is depicted sequentially as it transitions from the LOAD state to the INJECT state. Common to all of FIGS. 3a-g, the view is a normal or axial view of the rotor-stator sealing plane, which permits the stator ports and stator port channels to be viewed simultaneously with the outlines of the rotor channels, such that their respective positional relationships may be observed. It will be understood that the sealing footprint of the rotor on the stator substantially precludes fluid communication between regions of the stator face or sealing plane at all locations other than where such communication is specifically enabled by the cooperative interaction of a rotor channel with stator ports or stator port channels.

Figure 3A:
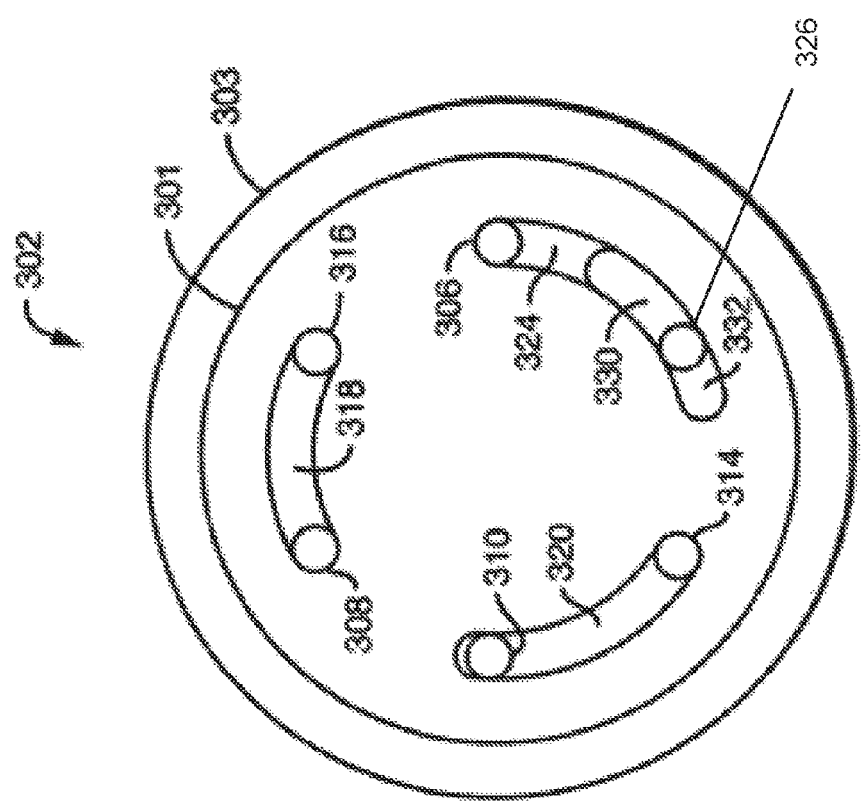
FIG. 3a is an axial view of a rotor-stator alignment of a valve in accordance with an embodiment of the invention in a LOAD state.

FIG. 3a depicts a planar rotary shear-seal injection valve 302 in an embodiment of the present invention. The valve rotor 301 is aligned with valve stator 303 to create flow paths in a LOAD state. The stator contains six ports which interface with features of the rotor at the rotor-stator sealing plane. These six stator ports are uniquely identified on the basis of their respective connectivities to system components external to the valve stator. A rotor sample channel 318 establishes connectivity between a sample needle port 308 and a downstream loop port 316 of an external sample loop. An upstream loop port 314 of the external sample loop is connected, through a rotor loop channel 320, to a syringe port 310. Rotor loop channel 320 extends beyond the syringe port 310 toward the sample channel 318.

The pump port 326, in the LOAD state, is in direct communication with the separation column port 306 through a rotor column channel 324. Rotor column channel 324 overlaps pump port 326 and has a rotor column channel extension 332 which extends clockwise toward rotor loop channel 320. On the stator, pump port 326 has a pump port channel 330 extending counter-clockwise along an arc toward column port 306.

Figure 3B:
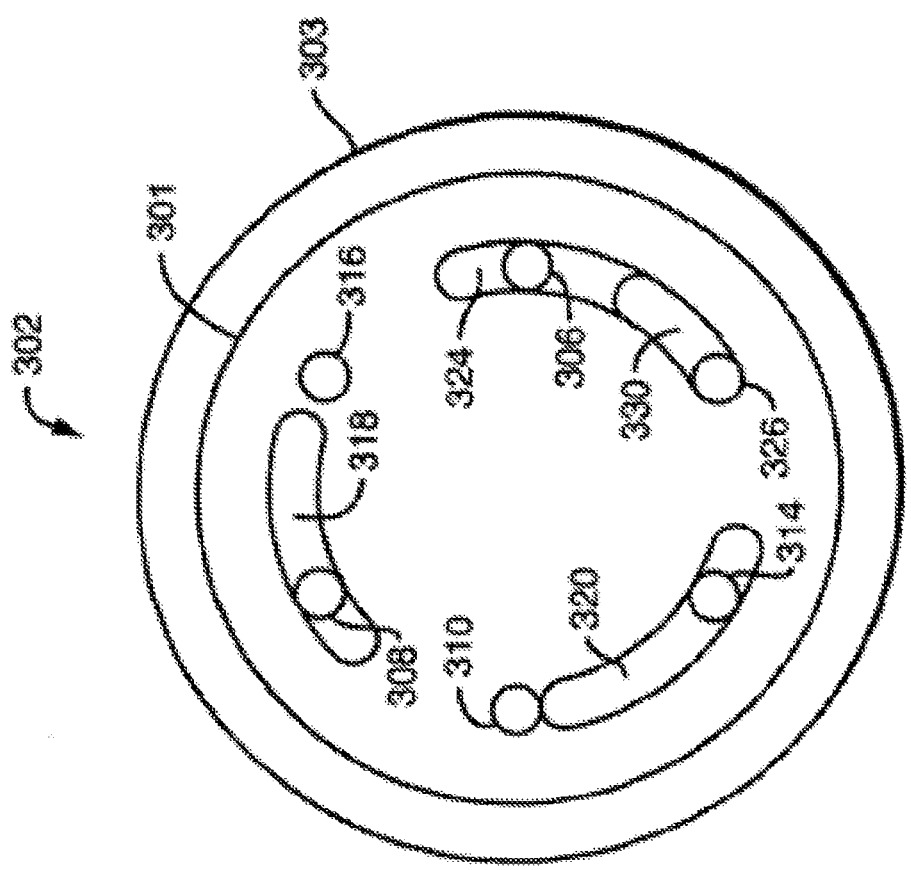
FIG. 3b is an axial view of a rotor-stator alignment of a valve depicted at 15 degrees counter-clockwise rotation in accordance with an embodiment of the invention.

During actuation of the valve from the LOAD state to the INJECT state, the rotor rotates counter-clockwise as shown in FIGS. 3b-f. FIG. 3b shows the valve rotor 301 rotated about 15 degrees counter-clockwise. The pump port 326 remains in fluid communication with separation column port 306 through rotor column channel 324. The sample loop is fully isolated at downstream loop port 316 from any other stator ports, whereas the sample loop has just achieved isolation at upstream loop port 314 from syringe port 310. When the valve is eventually returned to the LOAD state, during which process the valve rotor 301 is actuated clockwise back to the orientation shown in FIG. 3a, this rotor channel configuration allows the pressurized mobile phase within the sample loop to be decompressed with the discharge current directed toward the syringe port 310 rather than toward the sample needle port 308. Since pump-to-column fluid communication is maintained through column channel 324, the valve rotor can be arrested in this position, allowing time for the syringe assembly to actively decompress or vent the excess pressure.

Figure 3C:
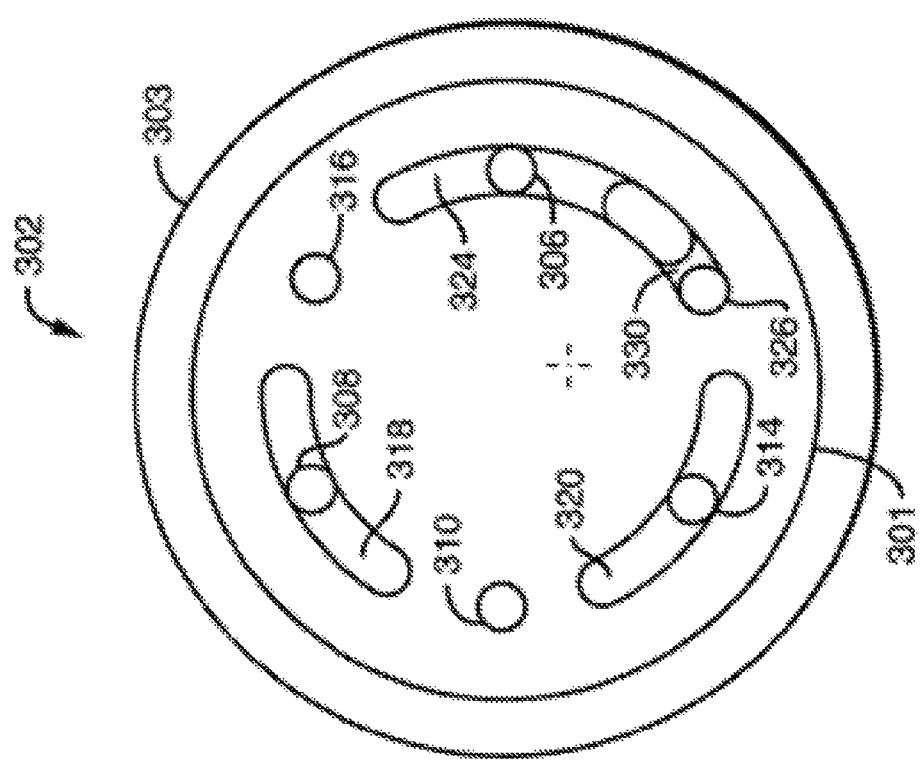
FIG. 3c is an axial view of a rotor-stator alignment of a valve depicted at 30 degrees counter-clockwise rotation in accordance with an embodiment of the invention.

FIG. 3c depicts an embodiment of the present invention with the rotor in transition at about 30 degrees counter-clockwise relative to the LOAD state orientation. Pump port 326 remains in direct communication with the separation column port 306 through pump stator channel 330 and rotor column channel 324. The sample loop is fully isolated at both the upstream loop port 314 and the downstream loop port 316. The syringe port 310 and the sample needle port 308 are also isolated.

FIG. 3d depicts an embodiment of the present invention with the rotor in transition at about 45 degrees counter-clockwise rotation relative to the LOAD state orientation. The pump port 326 remains in direct communication with the separation column port 306 through pump stator channel 330 and rotor column channel 324. The sample loop remains fully isolated at both the upstream loop port 314 and the downstream loop port 316. The syringe port 310 and the sample needle port 308 also remain isolated.

FIGS. 3e-f show an illustrative embodiment of the invention as it nears completion of the state transition from LOAD to INJECT. At about 50 degrees of counter-clockwise rotor rotation, as depicted in FIG. 3e, pump port 326 remains in direct fluid communication with separation column port 306 through pump stator channel 330 and rotor column channel 324. Additionally, pump port 326 establishes fluid communication with upstream loop port 314 and downstream loop port 316. Pump port 326 connects to upstream loop port 314 through rotor loop channel 320, substantially simultaneously connecting to downstream loop port 316 through rotor column channel 324. Note also that in the rotor orientation of FIG. 3e, fluid communication is established between syringe port 310 and sample needle port 308.

It is a further option to ensure that the sample loop is deterministically pressurized from the direction of upstream loop port 314. To accomplish this, a timing bias may be introduced through the incorporation of a small extension of rotor loop channel 320 directed counter clockwise toward pump port 326. Alternately, stator pump port 326 may be provided with a small stator channel extension which is directed clockwise toward upstream loop port 314. The purpose of either of the above extensions is to enable fluid communication to be established between pump port 326 and upstream loop port 314 with a timing lead of at least several milliseconds relative to the establishment of fluid communication between pump port 326 and downstream loop port 316. It will be appreciated that a timing lead of several milliseconds can be obtained by very subtle modification (by extension) of rotor loop channel 320 or stator pump port 326, or by a combined modification of the two.

As valve rotor 301 approaches the INJECT state, as shown in FIG. 3f at about 55 degrees counter-clockwise rotation, the valve rotor 301 terminates direct fluid communication between pump port 326 and separation column port 306 through column channel 324. Fluid communication between the pump port 326 and separation column port 306 is obtained through the sample loop, by the respective connection of pump port 326 with upstream loop port 314, and the connection of downstream loop port 316 with column port 306. The valve rotor 301 terminates the direct connection between the pump port 326 and separation column port 306, through column channel 324, only subsequent to the establishment of a flow path through the sample loop. The pump port 326 is in fluid communication with upstream loop port 314 through rotor loop channel 320. The separation column port 306 is in fluid communication with downstream loop port 316 of the sample loop through rotor column channel 324. Syringe port 310 remains in fluid communication with sample needle port 308 through rotor sample channel 318.

Figure 3G:
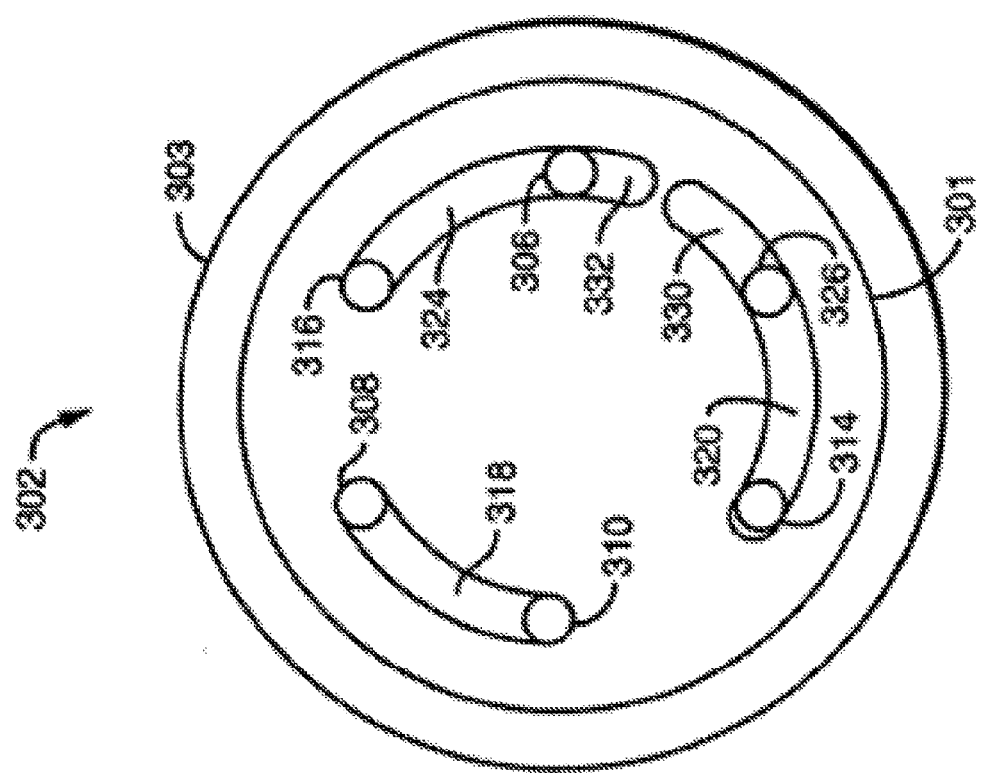
FIG. 3g is an axial view of a rotor-stator alignment of a valve depicted at 60 degrees counter-clockwise rotation in accordance with an embodiment of the invention, corresponding to the INJECT state of the valve.

FIG. 3g shows an illustrative embodiment of the present invention in the INJECT state, the valve rotor having rotated roughly 60 degrees counter-clockwise from the orientation corresponding to the LOAD state. Fluid communication between pump port 326 and separation column port 306 is exclusively through the sample loop. Pump port 326 is in fluid communication with upstream loop port 314 of the sample loop through rotor loop channel 320. Separation column port 306 is in fluid communication with downstream loop port 316 through rotor column channel 324. Syringe port 310 remains in fluid communication with sample needle port 308 through rotor sample channel 318.

The rotor column channel extension 322 and the stator pump channel 330 have been swept by mobile phase substantially throughout the valve actuation, minimizing the possibility for sample solution to be retained in the valve geometry extensions. The small isolation distance between the pump stator channel 330 and column port 306 is allowable in light of the fact that the pump port 326 and column port 306 reside at effectively the same pressure, i.e. the pressure drop across the sample loop is negligible.

The connectivity maintained between pump port 326 and separation column port 306 permits a substantially constant flow of mobile phase liquid through the HPLC system from the pump to the column, eliminating flow blockage intervals during actuation of valve rotor 301, and thereby eliminating the source of flow blockage transients which can have destructive impact upon chromatography columns.

Figure 4B:
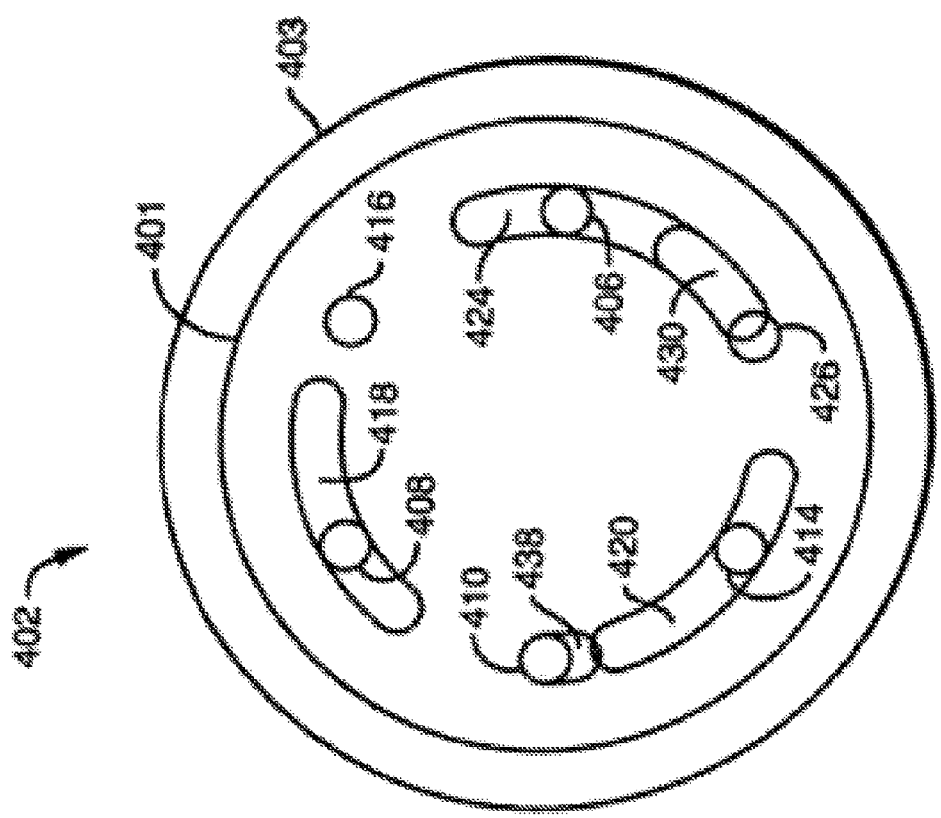
FIG. 4b is an axial view of a rotor-stator alignment of a valve in accordance with the present invention, depicted at 15 degrees counter-clockwise rotation.
Figure 4C:
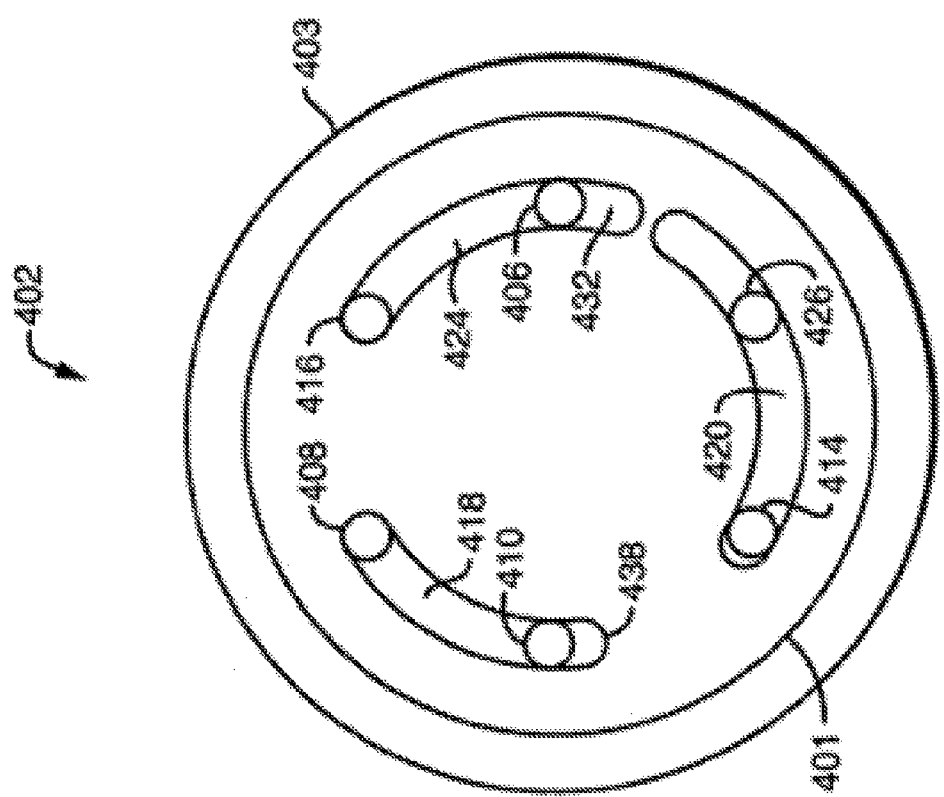
FIG. 4c is an axial view of a rotor-stator alignment of a valve in accordance with the present invention, depicted at 60 degrees counter-clockwise rotation corresponding to the INJECT state of the valve.

FIGS. 4a-c depict another illustrative embodiment according to the invention in which sample loop decompression is biased or preferentially directed toward the syringe port 410 by a modification to the syringe port which interacts cooperatively with a modification to rotor loop channel 420 to achieve a desired valve timing bias when the valve 402 is transitioned from the INJECT state to the LOAD state. FIGS. 4a-c sequentially depict the illustrative embodiment as it undergoes transition from the LOAD state to the INJECT state. Common to all of FIGS. 4a-c, the view is a normal or axial view of the rotor-stator sealing plane, which permits the stator ports and stator port channels to be viewed simultaneously with the outlines of the rotor channels, such that their respective positional relationships may be observed.

It will be understood that the sealing footprint of the rotor on the stator substantially precludes fluid communication between regions of the stator face or sealing plane at all locations other than where such communication is specifically enabled by the cooperative interaction of a rotor channel with stator ports or stator port channels.

FIG. 4a depicts valve rotor 401 aligned with valve stator 403 to create flow paths in a LOAD state. The stator contains six ports which interface with features of the rotor at the rotor-stator sealing plane. These six stator ports are uniquely identified on the basis of their respective connectivities to system components external to the valve stator. A rotor sample channel 418 establishes connectivity between a sample needle port 408 and a downstream loop port 416. An upstream loop port 414 is connected, through a rotor loop channel 420, to a syringe port 410. Rotor loop channel 420 extends beyond syringe port 410 in a clockwise direction toward sample channel 418. Syringe port 410 has a syringe port channel 438 in the stator extending counter-clockwise toward upstream loop port 414. Stator pump port 426, with the valve in the LOAD state, is in fluid communication with separation column port 406 through rotor column channel 424. Rotor column channel 424 overlaps pump port 426 and has an extension 432 which extends in a clockwise direction toward rotor loop channel 420. Pump port 426 has a pump stator channel 430 extending in a counterclockwise direction toward column port 406. In the rotor orientation of FIG. 4a, sample solution can be aspirated into the sample loop while the pump maintains delivery of mobile phase liquid to the column.

FIG. 4b shows the illustrative embodiment with the valve rotor 403 at roughly 15 degrees of rotation counter-clockwise from the LOAD state. The pump port 426 remains in direct communication with separation column port 406 through rotor column channel 424. The sample loop is isolated at downstream loop port 416, but remains in fluid communication with the syringe port 410 by way of upstream loop port 414. When the valve is eventually returned from the INJECT state back to the LOAD state, fluid communication between upstream loop port 414 and syringe port 410 is established prior to the establishment of fluid communication between downstream loop port 416 and sample needle port 408. This timing bias is achieved through the interaction of rotor loop channel 420 with syringe port channel 438 in the stator, and directs the fluid current associated with decompression of the sample loop contents toward syringe port 410.

With this configuration, decompression of the sample loop will normally cause a pressurization or partial charging of the fluid capacitance associated with the syringe assembly. Because pump-to-column flow remains enabled with the valve rotor in this intermediate position, the rotor motion can be temporarily arrested in this position, allowing the syringe assembly connected to syringe port 410 to actively decompress or vent the sample loop to achieve an internal pressure of substantially atmospheric pressure (0 PSIG). When valve rotor 403 is subsequently actuated to complete the transition of the valve to the LOAD state, fluid communication between downstream loop port 416 and sample needle port 408 is restored. Because substantially no pressure differential exists between downstream loop port 416 and sample needle port 408 when fluid communication is established between the two, an undesired displacement of liquid within the sample needle is avoided.

FIG. 4c shows the inventive valve in the INJECT state. Pump port 426 is in fluid communication with upstream loop port 414 through rotor loop channel 420. Separation column port 406 is in fluid communication with downstream loop port 416 through rotor column channel 424. The direct fluid communication between pump port 426 and column port 406 which existed by way of rotor column channel 424 and stator pump port channel 430 in FIGS. 4a and 4b is now blocked. Thus the fluid communication between the pump and column is exclusively through the sample loop, causing any sample solution within the sample loop to be flushed or swept toward the column. Syringe port 410 is in fluid communication with the sample needle port 408 through rotor sample channel 418.

The rotor column channel extension 432 and the stator pump port channel 430 are swept by the pump flow during actuation of the valve, minimizing the possibility for sample solution to be retained in the valve geometry extensions. The small isolation distance between pump port channel 430 and rotor column channel extension 432 is allowable in light of the fact that pump port 426 and column port 406 reside at substantially the same pressure, i.e. the pressure drop across the sample loop is negligible.

The connectivity maintained between pump port 426 and separation column port 406 during valve actuation permits a substantially constant flow of mobile phase liquid to be maintained through the HPLC system from pump to column, eliminating flow blockage intervals during actuation of valve rotor 401, and thereby eliminating the source of flow blockage transients which can have destructive impact upon chromatography columns.

FIGS. 5a-d depict an embodiment in accordance with the present invention in which an additional stator port (i.e., a seventh port) is utilized to pre-compress the contents of the sample loop to system operating pressure prior to transition of the valve 502 fully to the INJECT state. Common to all of FIGS. 5a-d, the view is a normal or axial view of the rotor-stator sealing plane, which permits the stator ports and stator port channels to be viewed simultaneously with the outlines of the rotor channels, such that their respective positional relationships may be observed. It will be understood that the sealing footprint of the rotor on the stator substantially precludes fluid communication between regions of the stator face or sealing plane at all locations other than where such communication is specifically enabled by the cooperative interaction of a rotor channel with stator ports or stator port channels.

FIG. 5a depicts valve rotor 501 aligned with valve stator 503 to create flow paths in a LOAD state. The stator contains seven ports which interface with features of the rotor at the rotor-stator sealing plane. These seven stator ports are identified on the basis of their respective connectivities to system components external to the valve stator. A rotor sample channel 518 establishes fluid communication between a sample needle port 508 and a downstream loop port 516. An upstream loop port 514 is in fluid communication with syringe port 510 through a rotor loop channel 520. Syringe port 510 has a syringe port channel 538 in the stator extending counter-clockwise toward upstream loop port 514. Rotor loop channel 520 extends beyond syringe port 510 in a clockwise direction toward rotor sample channel 518.

In the LOAD state of the valve, stator pump port 526 is in fluid communication with separation column port 506 through rotor column channel 524. Rotor column channel 524 overlaps pump port 526 and has a rotor column channel extension 532 which extends clockwise toward loop channel 520. Pump port 526 has a stator pump port channel 530 extending toward column port 506.

The additional stator port 534 is interposed in the stator between upstream loop port 514 and pump port 526. The additional stator port 534 communicates with the pump through a fluid conduit having a selected resistance to fluid flow. Such flow resistance can be manipulated by selection of the internal diameter and length of the fluid conduit used to connect additional stator port 534 to the pump. The fluid conduit connecting stator pump port 526 to the pump is normally dimensioned to minimize the resistance to flow, whereas the fluid conduit connecting additional stator port 534 to the pump is intentionally dimensioned to supply a resistance to flow in an amount as further discussed below.

In the LOAD state of the valve, pump port 526 and additional stator port 534 reside at substantially the same pressure, permitting a reduced isolation distance to exist between rotor column channel extension 532 and additional stator port 534, without impairing the overall sealing characteristics of the valve. In the LOAD state of the valve, mobile phase liquid flow from the pump is conveyed to the column exclusively through pump port 526.

Figure 5B:
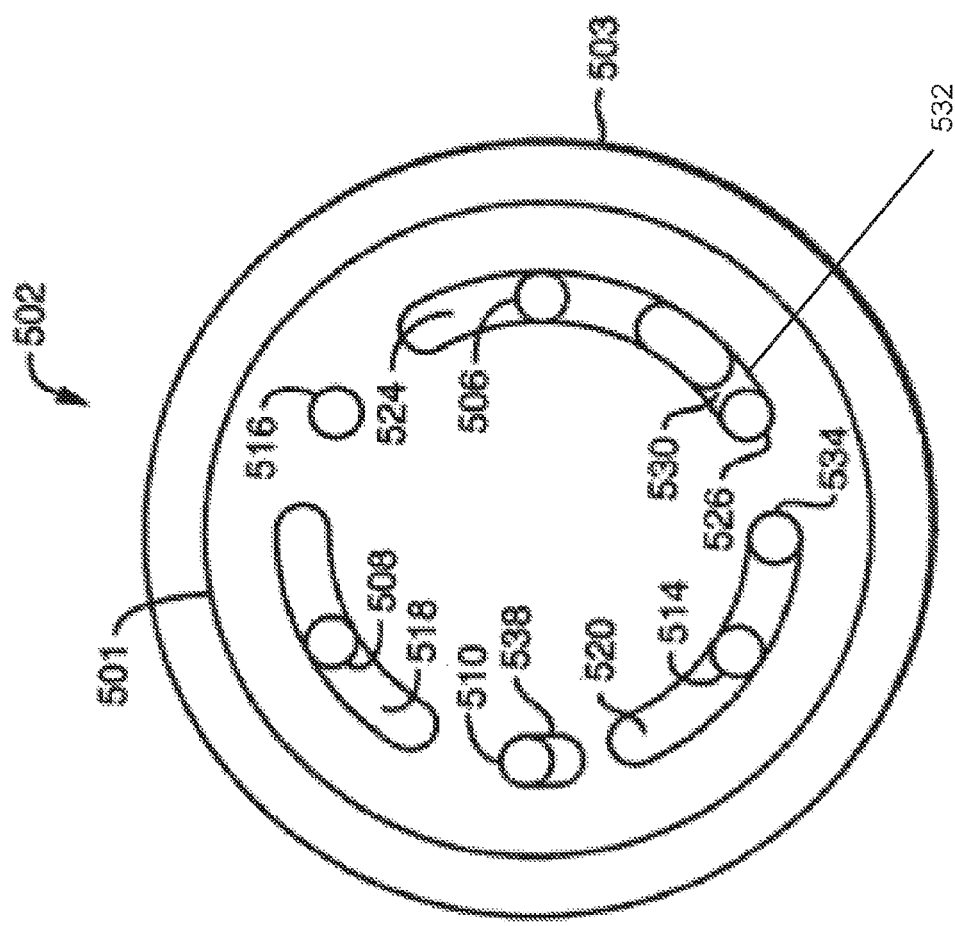
FIG. 5b is an axial view of a rotor-stator alignment of an illustrative embodiment of a loop-pre-compressing valve with a seventh port, in accordance with the present invention, depicted at 30 degrees counter-clockwise rotation.

FIG. 5b shows the illustrative embodiment at 30 degrees of counter-clockwise rotation of valve rotor 501. Pump port 526 is in direct fluid communication with separation column port 506 through the cooperative interaction of stator pump port channel 530 with rotor column channel 524 and rotor column channel extension 532. Syringe port 510 and sample needle port 508 are fluidically isolated, as is downstream loop port 516. Because pump-to-column flow remains enabled in this orientation of valve rotor 501, the rotor may be arrested in this orientation for any time interval deemed necessary in the context of the sample loop pre-compression discussed immediately below.

In the valve rotor orientation of FIG. 5b, rotor loop channel 520 causes upstream loop port 514 to be in fluid communication with additional stator port 534. This configuration allows the sample loop contents to be pressurized in a rate-limited manner, due to the selected resistance to fluid flow which is interposed in the fluid path connecting the pump with additional stator port 534. Specifically, establishment of fluid communication between upstream loop port 514 and additional stator port 534 causes a sample loop pressurization fluid circuit to be temporarily placed in parallel with the fluid circuit which is maintaining pump-to-column mobile phase flow.

In the inventive sample injector of FIGS. 5a-d, loop pressurization or charging of the loop fluidic capacitance occurs in a rate-limited manner in parallel with ongoing mobile phase delivery to the column. The magnitude of the loop charging current can be controlled by selection of the resistance interposed between the pump and additional stator port 534, such that the loop charging current can be made small with respect to the ongoing mobile phase delivery to the column. Correspondingly, the timeframe over which loop charging occurs will be lengthened, and can be made sufficiently long (for example, from approximately one to several seconds) that useful compensatory action can be taken by the pump.

An example of such a compensatory action would be the slight elevation of pump delivery flow rate during the sample loop charging interval such that the flow rate delivered to the column was substantially unperturbed. Compensation of the time-varying magnitude of the modest loop charging current could be accomplished in either a closed-loop or an open-loop manner as suits the application. The combination of a valve implementation which does not block pump-to-column flow with a rate-limited sample loop pre-compression results in a minimized injection transient for systems operating with relatively large loop capacitance.

FIG. 5c depicts the illustrative valve embodiment in the INJECT state at about 60 degrees of counter-clockwise rotation of valve rotor 501. Pump port 526 is in fluid communication with upstream loop port 514 through rotor loop channel 520. Upstream loop port 514 is also in fluid communication with additional stator port 534 through rotor loop channel 520. Separation column port 506 is in fluid communication with downstream loop port 516 through rotor column channel 524. Syringe port 510 is in fluid communication with sample needle port 508 through rotor sample channel 518. Rotor column channel extension 532 and stator pump port channel 530 are flushed or swept by the pump flow during valve actuation, minimizing the possibility for sample solution to be retained in the valve geometry extensions.

The small isolation distance between stator pump channel 530 and rotor column channel extension 532 is allowable in light of the fact that pump port 526 and separation column port 506 reside at effectively the same pressure, i.e. the pressure drop across the sample loop is negligible. The additional stator port 534 is flushed by the system flow at a low rate consistent with the ratio of resistances of the respective fluid paths connecting pump port 526 and additional stator port 534 to the pump. The resistances and volumes of these two parallel paths may be selected such that the flushing or purging times of the two are substantially matched, thereby reducing the potential for disruption of a compositional gradient profile.

Figure 5D:
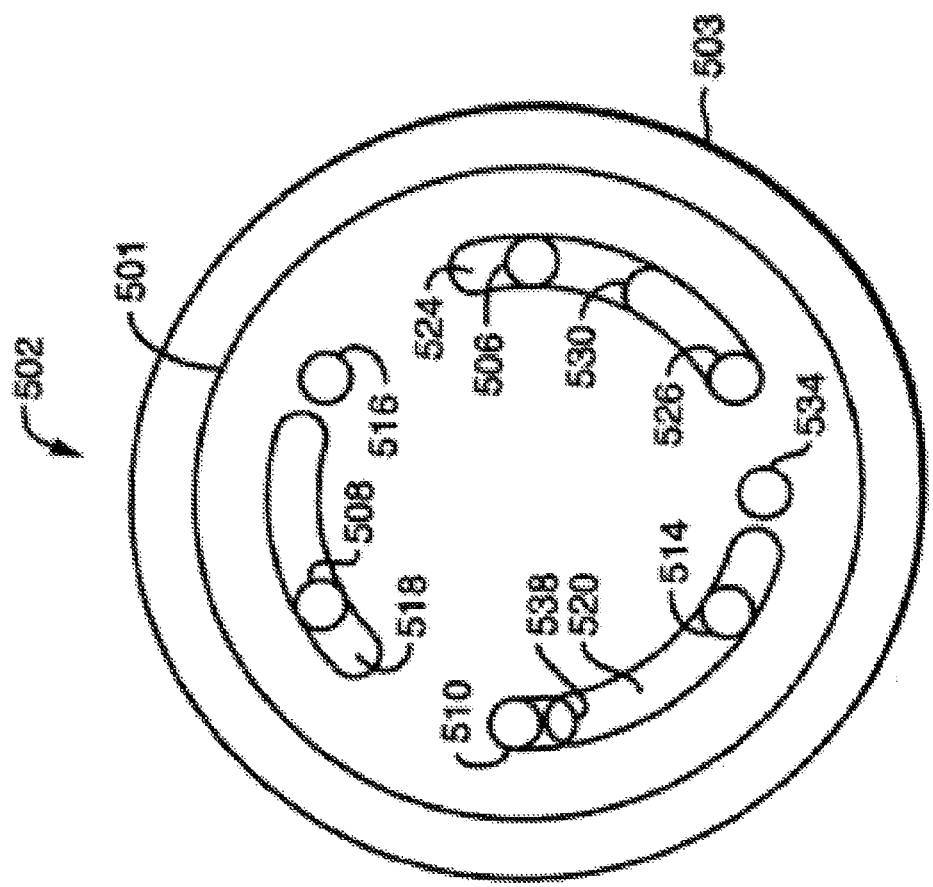
FIG. 5d is an axial view of a rotor-stator alignment of an illustrative embodiment of a loop-pre-compressing valve with a seventh port, in accordance with the present invention, depicted at loop decompression as the valve returns to the LOAD state.

FIG. 5d depicts the illustrative embodiment at a point during the recovery of the valve from the INJECT to the LOAD state. Pump port 526 is in fluid communication with separation column port 506 through rotor column channel 524. Downstream loop port 516 is not yet in fluid communication with sample needle port 508, whereas upstream loop port 514 is now in fluid communication with syringe port 510, due to the interaction of rotor loop channel 520 with syringe port channel 538 in the stator. The timing bias introduced by the interaction of rotor loop channel 520 with syringe port channel 538 allows the internal pressure of the sample loop to be discharged toward the syringe port 510 rather than toward the sample needle port 508.

The presence of additional stator port 534 does not interfere with the ability to achieve decompression of the sample loop toward syringe port 510 during recovery of the valve from the INJECT to the LOAD state.

Figure 6A:
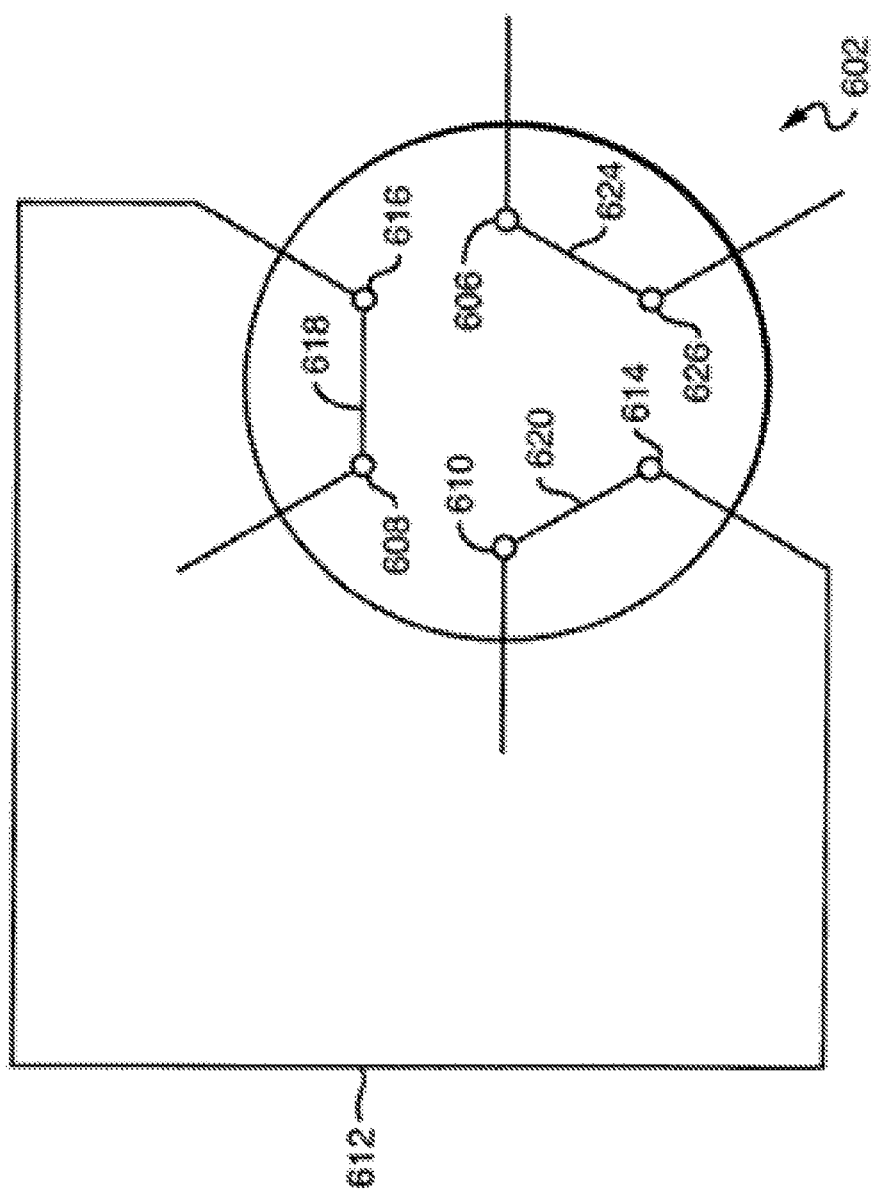
FIG. 6a is a schematic view of an illustrative embodiment of a valve, in accordance with the prior art, depicting the flow paths corresponding to the LOAD state of the valve.
Figure 6B:
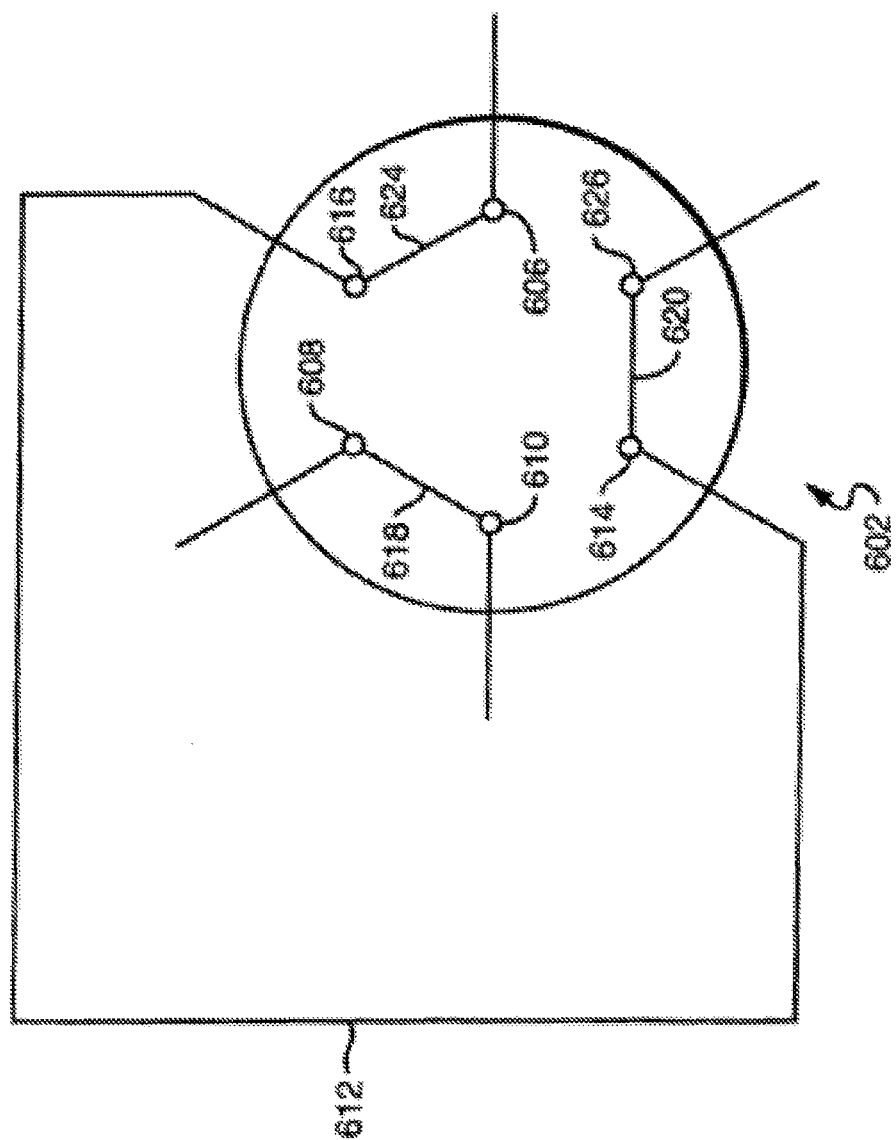
FIG. 6b is a schematic view of an illustrative embodiment of a valve, in accordance with the prior art, depicting the flow paths corresponding to the INJECT state of the valve.
Figure 7A:
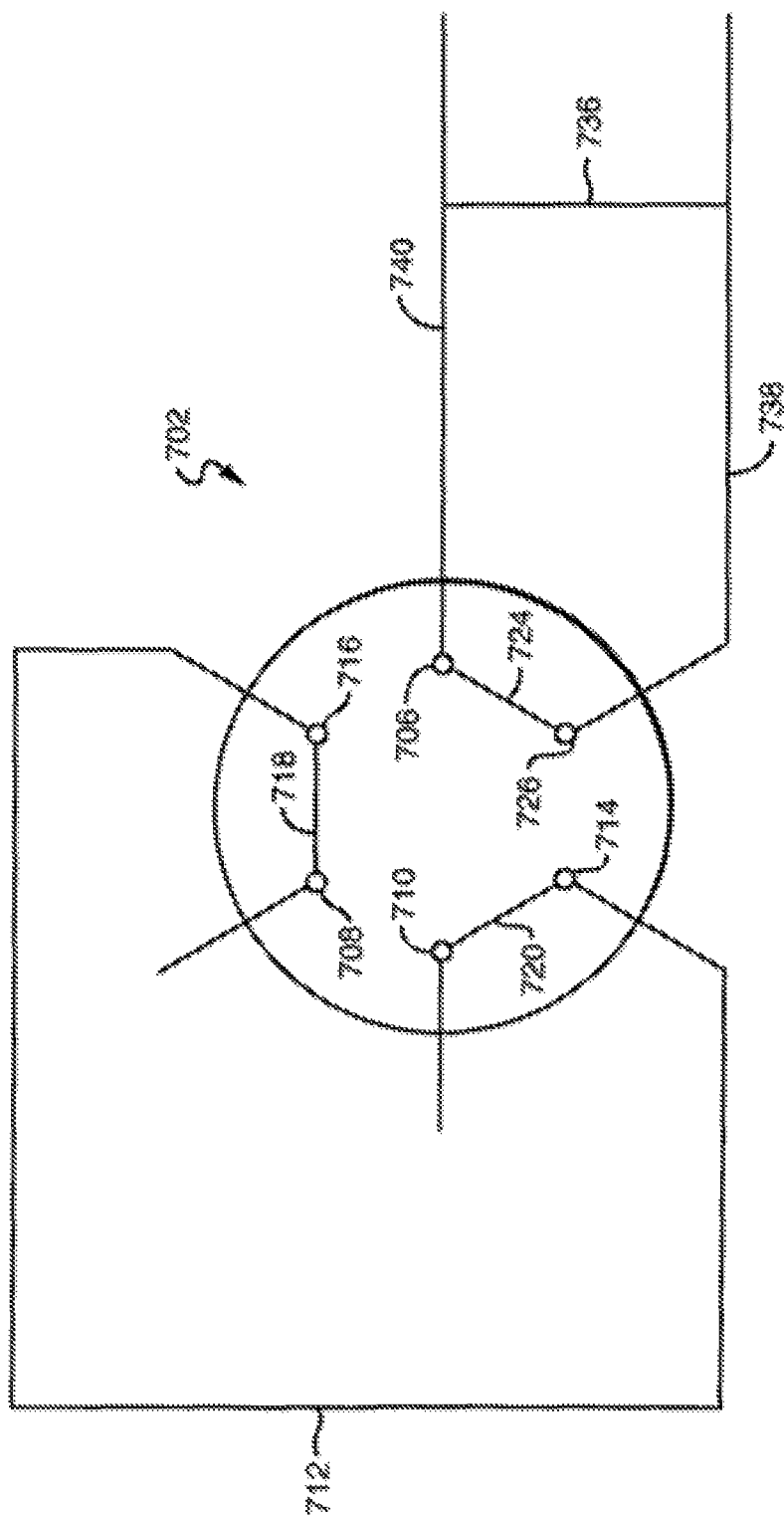
FIG. 7a is a schematic view of an illustrative embodiment of a valve incorporating a bypass channel in accordance with the present invention, depicting the flow paths corresponding to the LOAD state of the valve.
Figure 7B:
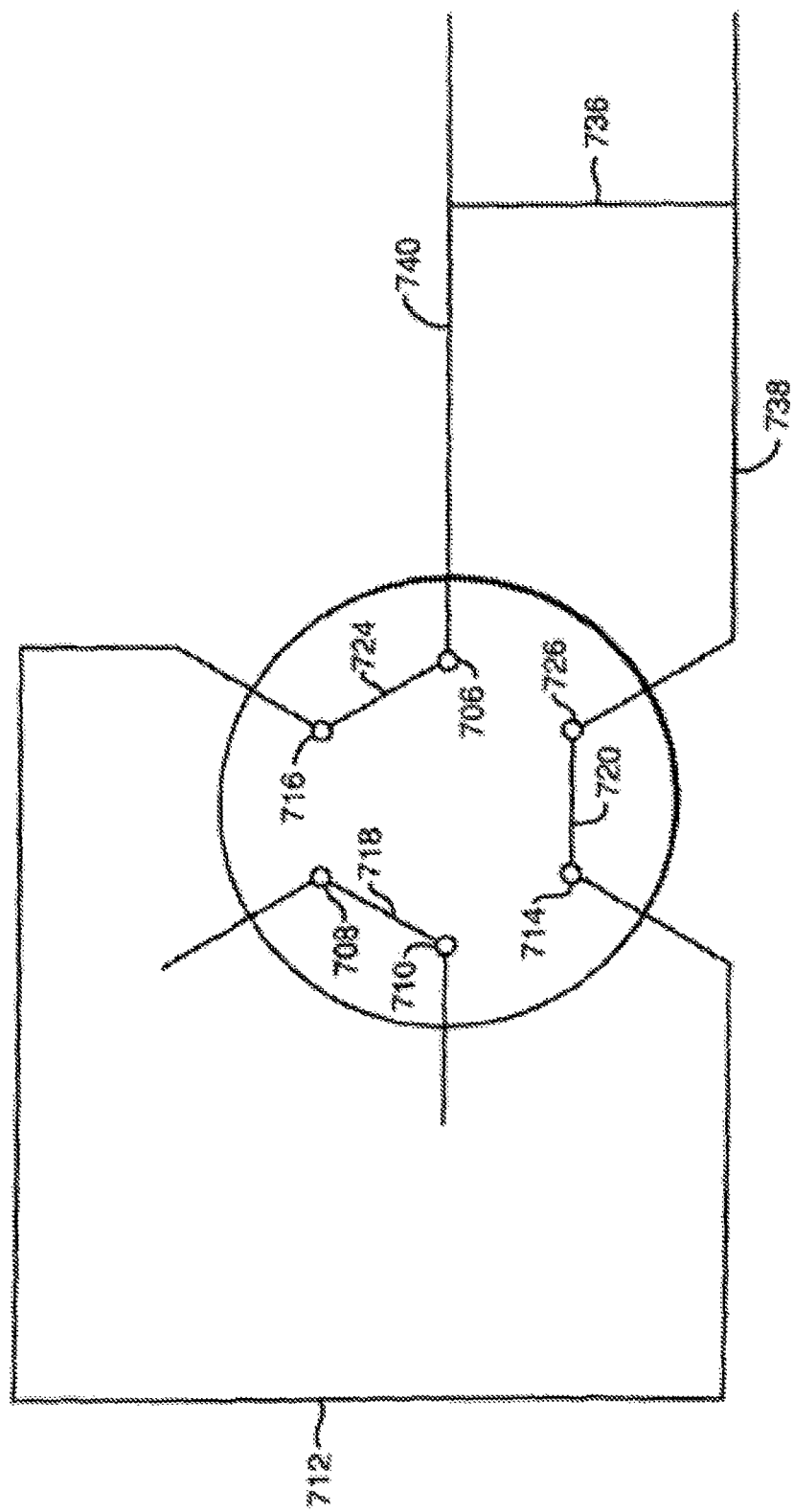
FIG. 7b is a schematic view of an illustrative embodiment of a valve incorporating a bypass channel in accordance with the present invention, depicting the flow paths corresponding to the INJECT state of the valve.

FIGS. 6a and 6b disclose a schematic representations of a prior-art rotary shear seal injection valve, and are intended for comparison with FIGS. 7a and 7b where a rotary shear seal injection valve is augmented with a pump-to-column bypass in accordance with an embodiment of the present invention. Common to all of FIGS. 6a-b and 7a-b, the stator ports are uniquely identified on the basis of their respective connectivities to system components external to the valve stator.

Turning to FIG. 6a, a standard rotary shear seal injection valve 602 is depicted in the LOAD state. A rotor sample channel 618 establishes connectivity between a sample needle port 608 and a downstream loop port 616 of sample loop 612. An upstream loop port 614 of sample loop 612 is connected, through rotor loop channel 620, to a syringe port 610. Stator pump port 626, in the LOAD state of the valve, is in fluid communication with the separation column port 606 through rotor column channel 624. In this rotor orientation, sample may be aspirated into sample loop 612 while mobile phase flow delivery is maintained to the column.

FIG. 6b depicts the same prior-art rotary shear seal injection valve 602 in the INJECT state. Pump port 626 is in fluid communication with upstream loop port 614 of sample loop 612 through rotor loop channel 620. Separation column port 606 is in fluid communication with downstream loop port 616 of sample loop 612 through rotor column channel 624. Thus fluid communication between pump port 626 and separation column port 606 is obtained by way of sample loop 612. In this rotor orientation, sample which was aspirated into sample loop 612 while the valve was in the LOAD state is flushed or swept toward the column by the mobile phase delivery of the pump. Syringe port 610 is in fluid communication with sample needle port 608 through rotor sample channel 618.

In FIG. 7a, the schematic of a sample injector according to the invention depicts a rotary shear seal injection valve 702 in conjunction with a bypass channel 736 which provides an additional path for fluid communication between pump port 726 and separation column port 706. The rotary shear seal valve embodiment may further incorporate rotor channel modifications and stator port or stator port channel modifications as described hereinbefore with respect to FIG. 3a-3g, 4a-4c, or 5a-d. In the LOAD state of the valve as shown in FIG. 7a, rotor sample channel 718 establishes fluid communication between sample needle port 708 and downstream loop port 716 of sample loop 712.

Upstream loop port 714 of sample loop 712 communicates, through rotor loop channel 720, to syringe port 710. Pump port 726, in the LOAD state, is in direct communication with separation column port 706 through rotor column channel 724. The bypass channel 736 is connected to pump port 726 through pump tubing 738 and to separation column port 706 through column tubing 740. In this valve rotor orientation, sample may be aspirated into sample loop 712 while mobile phase flow delivery is maintained to the column. In this illustrative embodiment, bypass channel 736 generates a resistance to mobile phase flow as a function of its internal diameter and length. In the LOAD state of the valve, bypass channel 736 resides in parallel with a second fluid circuit comprising rotor column channel 724, pump tubing 738, and column tubing 740.

The latter fluid circuit is dimensioned so as to have a resistance to flow which is low relative to that of bypass channel 736. The existence of this second, low-resistance, fluid circuit in parallel with bypass channel 736 when the valve is in the LOAD state yields a different behavior from the resistive bypass implementation of Abrahams and Hutchins. In the inventive sample injector of FIG. 7*a*, the bypass path does not carry 100 percent of the mobile phase flow while the valve is in the LOAD state. To the contrary, most of the mobile phase flow is shunted past bypass channel 736 in this valve state. As a result, the overall system resistance to flow is not increased appreciably when the injection valve is in the LOAD state.

FIG. 7*b* shows the embodiment of FIG. 7*a* with the shear seal valve in the INJECT state. Pump port 726 is in fluid communication with upstream loop port 714 of sample loop 712 through rotor loop channel 720. Separation column port 706 is in fluid communication with downstream loop port 716 of sample loop 712 through rotor column channel 724. Syringe port 710 is in fluid communication with sample needle port 708 through rotor sample channel 718. Thus in the INJECT state of the valve, bypass channel 736 resides in parallel with a second fluid circuit comprising pump tubing 738, rotor loop channel 720, sample loop 712, rotor column channel 724, and column tubing 740. The latter fluid circuit is dimensioned so as to have a resistance to flow which is low relative to that of bypass channel 736. In one illustrative embodiment of the invention, the resistance to flow of the bypass channel is approximately 32 times higher than the resistance to flow exhibited by the sample loop fluid circuit. This ratio of resistances for the two fluid circuits ensures that the majority of mobile phase flow is delivered through the sample loop path with the valve in the INJECT state.

The existence of bypass channel 736 enables sample injection to be performed without causing blockage of mobile phase flow during valve state transition. Destructive pressure and flow rate transients associated with mobile phase flow blockage by the injection valve are thereby avoided. The existence of a significantly lower-resistance path in parallel with bypass 736 in both the LOAD and the INJECT states of the sample injector substantially eliminates a behavior where the system exhibits a differing resistance to flow based on whether it is residing in the LOAD or the INJECT state. Further, the six-port valve configuration of FIGS. 7*a-b* can be augmented with an interposed seventh port as detailed in FIGS. 5*a-d* to additionally preclude transients arising from sample loop charging, which can become significant when operating at high system pressures or with large sample loop capacitance. The bypass channel of FIGS. 7*a-b* can be applied to internal loop injection valves of the four port configuration, again by bypassing between the pump tubing and column tubing.

It will be recognized that it is an option to implement the bypass channel and its associated junctions in discrete components (tubes, fittings) external to the valve body, or to implement the channel and its junctions as a fluid circuit integrated within the body of the valve, or to utilize a combination of the two approaches.

Figure 8:
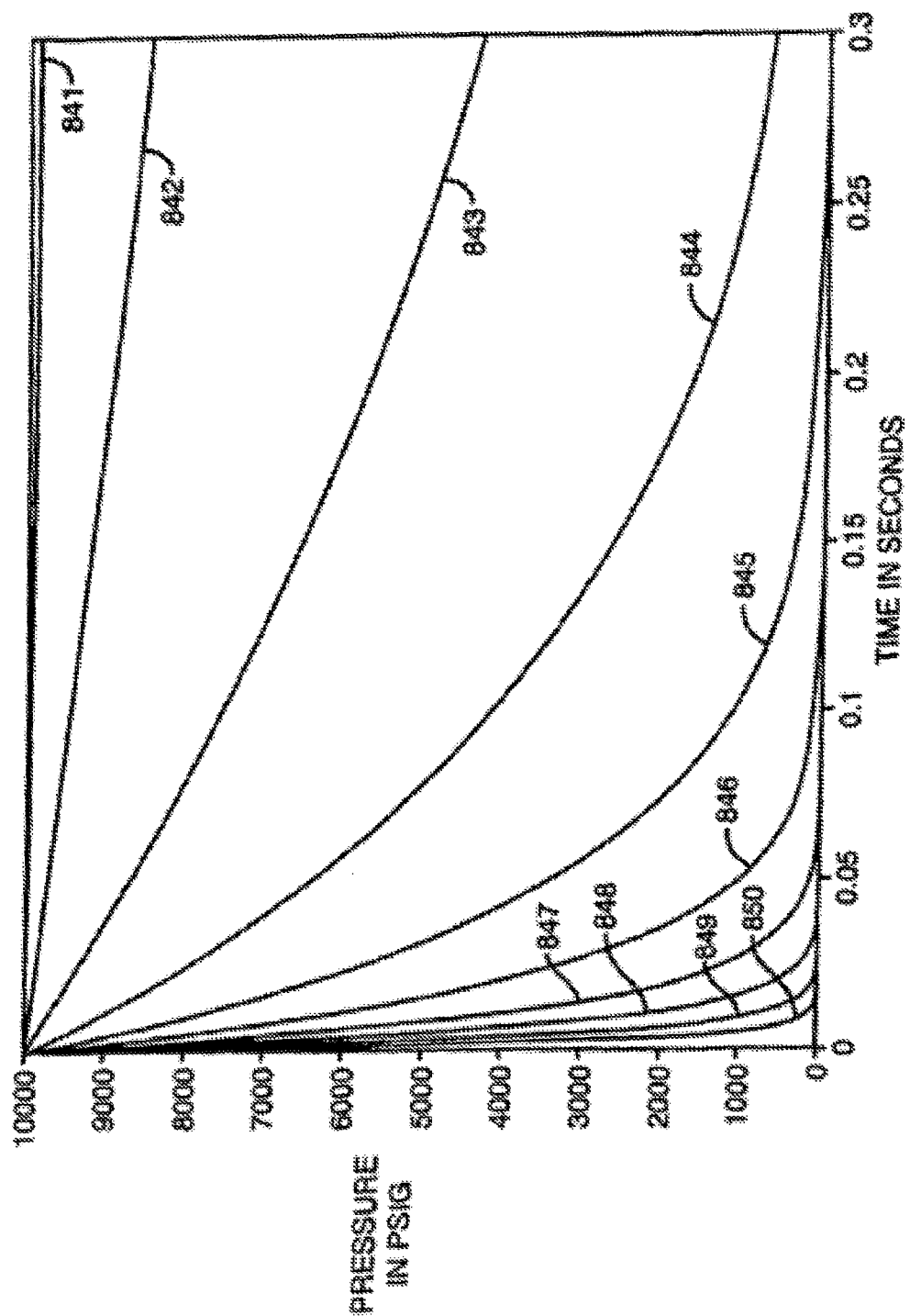
FIG. 8 is a graph depicting respective profiles of pressure decay achieved when a specified pump fluidic capacitance, which has been charged to an initial elevated pressure, is discharged through a fluid conduit of a defined length, where the conduit is further specified as having one of ten selected respective internal diameters.

Minimization of the exposure of the chromatography column to damaging transients can be further ensured by managing attributes of the fluid circuit upstream and downstream of a sample injection valve. Specifically, it is desirable to ensure that, to the extent possible, fluid currents associated with the transient charging of fluid capacitances are sourced by the pump as opposed to being sourced by the column. To achieve this biasing, the system designer can utilize the resistance to fluid flow of the fluid conduits upstream and downstream of the sample injection valve, configuring those fluid conduits such that a useful ratio of resistances is obtained for the purpose of protecting the column. In an illustrative embodiment, the resistance to flow exhibited by the fluid conduit interconnecting the injector and column is configured to be at least three times greater than the resistance to flow exhibited by the fluid conduit interconnecting the pump and injector. For any mobile phase which is traversing both the upstream (pump-to-injector) and downstream (injector-to-column) pathways, a ratio of resistances can be established by manipulation of the respective tubing lengths, tubing internal diameters, or both. FIG. 8 illustrates the discharge of a pump capacitance through a defined length of tubing, where the tubing internal diameter has been selected to be one of ten values. Trace 841 of FIG. 8 corresponds to the use of a nominal 0.001" (25.4 micrometer) internal diameter, with successive traces 842 through 850 corresponding to the selection of respective tubing internal diameter values from 0.002" to 0.010" (50.8 to 254.0 micrometers). The individual traces represent respective step responses of a predominantly R-C system where the characteristic hydraulic time constant has been manipulated primarily by manipulation of the resistance term.

It will be noted that with tubing diameters in the lower end of the diameter range (for example, traces 841 through 844), the time constant is too long to provide satisfactory short-term transient response. That is, the pump capacitance is not usefully available to satisfy a transient charging requirement at the injector. As the tubing internal diameter in this embodiment is increased to 0.009" (228.6 micrometers) (trace 849) or 0.010" (254.0 micrometers) (trace 850), the pump is now able to deliver a useful response within a few-millisecond timeframe. A similar approach to governing transient response can be applied to the injector-to-column fluid circuit, although with the opposing intent of making the hydraulic time-constant as long as is practical, thereby limiting the extent to which a column capacitance is discharged when a transient charging requirement exists elsewhere in the fluid circuit upstream of the column.

Although the embodiments discussed herein describe a single stator channel extension from the pump port towards the separation column port to extend the pump-to-column connectivity, it should be appreciated by those skilled in the art that such pump-to-column connectivity may be accomplished by additional channel extensions from the port, e.g. dual extensions extending oppositely from the pump port, establishing a prolonged connection between the pump and column.

Although the embodiments discussed herein describe a rotor having two extended channels creating flow paths through the valve, or alternatively one extended rotor channel in combination with an elongated stator port, those skilled in the art should appreciate that such biasing may be accomplished in accordance with the invention utilizing modifications to other stator ports or rotor channels.

Although the illustrative embodiments have been described herein with reference to "counter-clockwise" rotor rotation to accomplish a specified valve state transition, it should be appreciated that such state transitions can be effected by clockwise rotation of the valve in an alternative configuration.

Although the embodiments discussed herein have been described in terms of the incorporation of a planar rotary shear seal valve, it should be appreciated by those skilled in the art that the inventive sample injector could be realized with a rotary shear seal valve having a conical or cylindrical form (often referred to as a rotary spool type of valve), or with a shear seal valve having a linear or other form. Likewise, while the shear seal valve approach in general facilitates a useful degree of integration of valve elements, allowing a compact sample injector with relatively simple actuation requirements, it should be recognized that the inventive sample injector could be realized with a plurality of diaphragm, pin, or other type valve elements, or with a combination of types of valve elements as suits the application.

Although the implementation of flow restriction in the illustrative embodiments described herein is accomplished by the selection of a tubing internal diameter and tubing length, it should be appreciated that other means of implementing flow restriction are available, such as alternative internal geometries, internal coatings, discrete flow restrictors, or the like.

Although the pre-compression of the sample loop contents prior to actual injection of the sample into the pump-to-column mobile phase stream has been described in the illustrative embodiments described herein using the chromatography pump as the source of the fluid current used for pre-compression, it should be appreciated by those skilled in the art that an alternate pressure source may be used to supply this fluid current, such as an auxiliary pump.

Although the illustrative embodiments discussed herein have been described in the context of performing a substantially direct injection of sample onto an analytical column, it should be appreciated by those skilled in the art that the inventive sample injector could be applied in sample trapping applications or in other modes of chromatography where sample injection is performed onto a trapping column, cartridge, or other receiving device downstream of the sample injector.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A rotary shear-seal injection valve comprising:
    a stator having a plurality of stator ports, at least one of said stator ports being in fluid communication with a pump; and
    a rotor rotatably abutting said stator, said rotor having a plurality of channels fluidly connecting at least two of the stator ports, the plurality of channels and plurality of stator ports being configured to maintain a first flow path from the pump to a column during a valve transition from a load state to an inject state while establishing a second flow path through the valve between a syringe port and a sample needle port.

2. The rotary shear-seal injection valve of claim 1 further comprising:
    a first stator channel for fluidly connecting the pump to the column.

3. The rotary shear-seal injection valve of claim 2 further comprising:
    a syringe port channel having a sufficient length to ensure the fluid flow in the sample loop is discharged towards a syringe during valve reversion.

4. The rotary shear-seal injection valve of claim 3 wherein,
    at least a second one of said stator ports is in fluid communication with the pump such that, during valve transition from the load state to the inject state, the second stator port becomes fluidly connected to an upstream side of a sample loop and the pump concurrently pressurizes the sample loop and the first flow path.

5. The rotary shear-seal injection valve of claim 2, wherein:
    at least a second one of said stator ports is in fluid communication with the pump such that, during valve transition from the load state to the inject state, the second stator port becomes fluidly connected to an upstream side of a sample loop and the pump concurrently pressurizes the sample loop and the first flow path.

6. The rotary shear-seal injection valve of claim 1 further comprising:
    a stator channel extension for fluidly connecting the pump to a sample loop.

7. The rotary shear-seal injection valve of claim 6 further comprising:
    a syringe port channel having a sufficient length to ensure the fluid flow in the sample loop is discharged towards a syringe during upon valve reversion.

8. The rotary shear-seal injection valve of claim 7 wherein,
    at least a second one of said stator ports is in fluid communication with the pump such that, during valve transition from the load state to the inject state, the second stator port becomes fluidly connected to an upstream side of the sample loop and the pump concurrently pressurizes the sample loop and the first flow path.

9. The rotary shear-seal injection valve of claim 6 wherein,
    at least a second one of said stator ports is in fluid communication with the pump such that, during valve transition from the load state to the inject state, the second stator port becomes fluidly connected to an upstream side of the sample loop and the pump concurrently pressurizes the sample loop and the first flow path.

10. The rotary shear-seal injection valve of claim 1 further comprising:
    a channel having a length sufficient to ensure the fluid flow in a sample loop is discharged towards a syringe during valve reversion.

11. The rotary shear-seal injection valve of claim 10 wherein,
   at least a second one of said stator ports is in fluid communication with the pump such that, during valve transition from the load state to the inject state, the second stator port becomes fluidly connected to an upstream side of the sample loop and the pump concurrently pressurizes the sample loop and the first flow path.

12. The rotary shear-seal injection valve of claim 1 further comprising:
   a syringe port channel having a sufficient length to ensure the fluid flow in a sample loop is discharged towards a syringe during valve reversion.

13. The rotary shear-seal injection valve of claim 12 wherein,
   at least a second one of said stator ports is in fluid communication with the pump such that, during valve transition from the load state to the inject state, the second stator port becomes fluidly connected to an upstream side of the sample loop and the pump concurrently pressurizes the sample loop and the first flow path.

14. The rotary shear-seal injection valve of claim 1, wherein:
   at least a second one of said stator ports is in fluid communication with the pump such that, during the valve transition from the load state to the inject state, the second stator port becomes fluidly connected to an upstream side of a sample loop and the pump concurrently pressurizes the sample loop and the first flow path.

* * * * *